(12) United States Patent
Yamshchikov

(10) Patent No.: US 7,455,842 B2
(45) Date of Patent: Nov. 25, 2008

(54) CHIMERIC WEST NILE VIRUSES AND USES THEREOF

(75) Inventor: Vladimir F. Yamshchikov, Olathe, KS (US)

(73) Assignee: University of Kansas, Lawrence, KS (US)

( * ) Notice: Subject to any disclaimer, the term of this patent is extended or adjusted under 35 U.S.C. 154(b) by 100 days.

(21) Appl. No.: 11/294,178

(22) Filed: Dec. 5, 2005

(65) Prior Publication Data

US 2007/0128711 A1 Jun. 7, 2007

(51) Int. Cl.
- A61K 39/12 (2006.01)
- A61K 48/00 (2006.01)
- C12N 5/10 (2006.01)
- C12N 7/01 (2006.01)
- C12N 15/40 (2006.01)

(52) U.S. Cl. .............. 424/199.1; 424/218.1; 424/204.1; 424/205.1; 435/235.1; 435/320.1; 435/325; 536/23.72; 514/44

(58) Field of Classification Search .............. 435/235.1, 435/5; 424/218.1, 202.1, 204.1, 199.1, 93.2, 424/186.1
See application file for complete search history.

(56) References Cited

U.S. PATENT DOCUMENTS 7,094,411 B2 * 8/2006 Kinney et al. ............ 424/218.1

2005/0163804 A1 * 7/2005 Chang ...................... 424/218.1
2005/0276816 A1   12/2005 Yamshchikov

FOREIGN PATENT DOCUMENTS

WO    WO 9306214 A1 *  4/1993

OTHER PUBLICATIONS

Beasley et al., "Envelope Glycoprotein Glycosylation Status Influences Mouse Neuroinvasion Phenotype of Genetic Lineage 1 West Nile Virus Strains," Journal of Virology, vol. 79, No. 13 (Jul. 2005).*
Petersen et al., "West Nile Virus: A Reemerging Global Pathogen," Emerging Infectious Diseases, vol. 7, No. 4 (2001).*
Yamshchikov, et al., (2004). An attenuated West Nile prototype virus is highly immunogenic and protects against the deadly NY99 strain: a candidate for live WN vaccine development. *Virology 330*, 304-312.
Yamshchikov, et al., (2001a). A new strategy in design of +RNA virus infectious clones enabling their stable propagation in *E. coli*. *Virology 281*, 272-280.
Yamshchikov, et al., (2001b). An infectious clone of the West Nile flavivirus. *Virology 281*, 294-304.

* cited by examiner

*Primary Examiner*—Mary R. Mosher
*Assistant Examiner*—Stuart W Snyder
(74) *Attorney, Agent, or Firm*—Stinson Morrison Hecker LLP

(57) ABSTRACT

A chimeric West Nile live virus comprised of the NY99 and WN1415 strains and an infectious DNA recombinant construct encoding for the chimeric virus are provided, as well as immunogenic compositions and their method of use.

23 Claims, 5 Drawing Sheets

SEQUENCE LISTING

<160> NUMBER OF SEQ ID NOS: 11

<210> SEQ ID NO 1
<211> LENGTH: 15
<212> TYPE: DNA
<213> ORGANISM: Infectious DNA of West Nile virus with Thymidine Spacer

<400> SEQUENCE: 1
gaaccgagta gttcg                                                    15

<210> SEQ ID NO 2
<211> LENGTH: 13
<212> TYPE: DNA
<213> ORGANISM: Infectious DNA of West Nile virus with Thymidine Spacer

<400> SEQUENCE: 2
gaaccgtagt agt                                                      13

<210> SEQ ID NO 3
<211> LENGTH: 17
<212> TYPE: DNA
<213> ORGANISM: Infectious DNA of West Nile virus with Thymidine Spacer

<400> SEQUENCE: 3
gaaccgttag tagttcg                                                  17

```
<210> SEQ ID NO 4
<211> LENGTH: 26
<212> TYPE: DNA
<213> ORGANISM: Infectious DNA of West Nile virus
<220> FEATURE:
<221> NAME/KEY: misc_feature
<223> OTHER INFORMATION: Direct Primer
<220> FEATURE:
<221> NAME/KEY: misc_feature
<223> OTHER INFORMATION: Direct Primer NY1414mD

<400> SEQUENCE: 4
gagtcgcacg gatcctactc cacaca                                              26

<210> SEQ ID NO 5
<211> LENGTH: 26
<212> TYPE: DNA
<213> ORGANISM: Infectious DNA of West Nile virus
<220> FEATURE:
<221> NAME/KEY: misc_feature
<223> OTHER INFORMATION: Reverse primer
<220> FEATURE:
<221> NAME/KEY: misc_feature
<223> OTHER INFORMATION: Reverse primer NY1439mR

<400> SEQUENCE: 5
tgtgtggagt aggatccgtg cgactc                                              26

<210> SEQ ID NO 6
<211> LENGTH: 30
<212> TYPE: DNA
<213> ORGANISM: Infectious DNA of West Nile virus
<220> FEATURE:
<221> NAME/KEY: misc_feature
<223> OTHER INFORMATION: Direct Primer
<220> FEATURE:
<221> NAME/KEY: misc_feature
<223> OTHER INFORMATION: Direct Primer NY1438delD

<400> SEQUENCE: 6
tcgcacggac aggttggagc cactcaggca                                          30

<210> SEQ ID NO 7
<211> LENGTH: 30
<212> TYPE: DNA
<213> ORGANISM: Infectious DNA of West Nile virus
<220> FEATURE:
<221> NAME/KEY: misc_feature
<223> OTHER INFORMATION: Reverse primer
<220> FEATURE:
<221> NAME/KEY: misc_feature
<223> OTHER INFORMATION: Reverse primer NY-1425delR

<400> SEQUENCE: 7
tccaacctgt ccgtgcgact ccacagtagt                                          30

<210> SEQ ID NO 8
<211> LENGTH: 12
<212> TYPE: DNA
<213> ORGANISM: Infectious DNA of West Nile virus

<400> SEQUENCE: 8
aactactcca ca                                                             12

<210> SEQ ID NO 9
<211> LENGTH: 30
<212> TYPE: DNA
<213> ORGANISM: Infectious DNA of West Nile virus
<220> FEATURE:
```

```
<221> NAME/KEY: misc_feature
<223> OTHER INFORMATION: Direct Primer
<220> FEATURE:
<221> NAME/KEY: misc_feature
<223> OTHER INFORMATION: Direct Primer NY1439delmD

<400> SEQUENCE: 9
tcgcacggaa agattggagc cactcaggca                                          30

<210> SEQ ID NO 10
<211> LENGTH: 30
<212> TYPE: DNA
<213> ORGANISM: Infectious DNA of West Nile virus
<220> FEATURE:
<221> NAME/KEY: misc_feature
<223> OTHER INFORMATION: Reverse primer
<220> FEATURE:
<221> NAME/KEY: misc_feature
<223> OTHER INFORMATION: Reverse primer NY1425delmR

<400> SEQUENCE: 10
tccaatcttt ccgtgcgact ccacagtagt                                          30

<210> SEQ ID NO 11
<211> LENGTH: 12
<212> TYPE: DNA
<213> ORGANISM: Infectious DNA of West Nile virus
<220> FEATURE:
<221> NAME/KEY: misc_feature
<223> OTHER INFORMATION: Glycosylation site encoding sequence

<400> SEQUENCE: 11
aactactcca ca                                                             12
```

CHIMERIC WEST NILE VIRUSES AND USES THEREOF

STATEMENT REGARDING FEDERALLY SPONSORED RESEARCH OR DEVELOPMENT

The present invention was sponsored by National Institute of Allergy and Infectious Disease Contracts No. AI049258 and AI052084, and the government may have certain rights in the invention.

CROSS-REFERENCE TO RELATED APPLICATIONS

Not Applicable.

BACKGROUND OF THE INVENTION

West Nile ("WN") virus was first isolated over 60 years ago from the blood of a febrile patient (Smithburn et al., 1940), and is one of the most widespread flaviviruses worldwide. The WN virus is endemic to Africa and has been repeatedly known in Europe and Asia for decades causing self-limiting epidemics and epizootics (Murgue et al., 2001; Savage et al., 1999). Recent introduction of the WN virus into the North American continent (Lanciotti et al., 1999) had disastrous consequences both for wildlife and human population (Roehrig et al., 2002), and in a few years, WN has developed into a nationwide epidemiological problem (CDC, 2005). In humans, WN infection is often inapparent or occurs as a mild febrile disease (Monath and Heinz, 1996). However, the WN virus has also associated with severe neurological symptoms (Flatau et al., 1981; Smithburn et al., 1940), and recent outbreaks of WN infection have been characterized by an increased CNS involvement (Roehrig et al., 2002; Solomon and Vaughn, 2002).

Based on serological data and genetic characterization, WN viruses have been grouped into at least two distinct lineages (Berthet et al., 1997; Price and O'Leary, 1967). Representatives with moderate and high virulence have been found in both WN virus groups (Beasley et al., 2002). Although highly related to certain strains circulating in the Middle East, the NY99 strain is perhaps the most pathogenic and virulent WN strain known to date (Monath, 2001). Recent studies have shown that mice that succumb to encephalitis after peripheral inoculation of NY99 in very small doses (Beasley et al., 2002).

The virions of the WN fever virus are spherical particles with a diameter of 50 nm constituted by a lipoproteic envelope surrounding an icosahedral nucleocapsid containing a positive polarity (+), single-strand RNA. A single open reading frame ("ORF") encodes all the viral proteins in the form of a polyprotein. The cleaving and maturation of this polyprotein leads to the production of about ten different viral proteins. The structural proteins are encoded by the 5' part of the genome and correspond to the nucleocapsid designated C (14 kDa), the envelope protein designated E (50 kDa), the pre-membrane protein designated prM (23 kDa), and the membrane protein designated M (7 kDa). The non-structural proteins are encoded by the 3' part of the genome and correspond to the proteins NS1 (40 kDa), NS2A (19 kDa), NS2B (14 kDa), NS3 (74 kDa), NS4A (15 kDa), NS4B (29 kDa), and NS5 (97 kDa).

In the mouse model, in which flaviviruses are inherently neurovirulent, both neurovirulence and neuroinvasiveness have been positively associated with determinants in the envelope proteins (Cecilia and Gould, 1991; Chambers et al., 1999; Gualano et al., 1998; Hasegawa et al., 1992; Holzmann et al., 1990; Holzmann et al., 1997; Jiang et al., 1993; McMinn, 1997; Pletnev et al., 1992; Pletnev et al., 1993). The envelope protein (E) of many flaviviruses is glycosylated, and while the WN virus is not an exception to this rule, a few non-glycosylated strains have been identified (Beasley et al., 2001; Berthet et al., 1997; Wengler et al., 1985). The importance of E protein glycosylation for expression of the virulent phenotype of lineage I WN viruses has been demonstrated experimentally (Beasley et al., 2005; Shirato et al., 2004). However, evidence documenting negative effects of E glycosylation on the WN virulence in mice or on its infectivity in cell cultures has been reported as well (Chambers et al., 1998; Hanna et al., 2005).

Currently, a number of subunit or recombinant WN vaccines for veterinary and human use are under development (Kahler, 2003; Lai and Monath, 2003; Ng et al., 2003; Nusbaum et al., 2003; Pletnev et al., 2002; Tesh et al., 2002). In contrast to subunit or inactivated vaccines, a live WN vaccine may be expected to elicit a long lasting balanced humoral and cell mediated immune response (Yamshchikov et al., 2005). However, the high virulence and pathogenicity of the NY99 strain (Beasley et al., 2002; Roehrig et al., 2002) makes it questionable for use in development of a live attenuated WN vaccine. Further, the known association of lineage I strains (such as the NY99 strain) with human and equine outbreaks (Lanciotti et al., 2002) raises a concern about their suitability for vaccine development in general. As such, there remains a need for the development of new live WN virus vaccines.

Recently, several (+) RNA virus studies have relied on the infectious clone methodology, which allows for targeted manipulation of viral genomes. In the "classical approach," (+) RNA viruses are recovered from cells transfected with synthetic RNA made by in vitro transcription of infectious clone cDNA templates. In a layered DNA/RNA approach, also known as "infectious DNA," the infectious (+) RNA viruses are recovered directly after transfection of plasmids carrying viral genome cDNA into susceptible cells. Unfortunately, difficulties are often encountered in the design of flavivirus infectious DNA. In addition, few studies have reported on the use of such infectious DNA constructs as a vaccine. Recently, applicant developed an infectious DNA construct encoding an attenuated WN virus denominated as WN1415 as described in co-pending patent application Ser. No. 11/065,783, which is incorporated by reference. Although the infectious DNA construct and virus may be useful as an immunogenic composition for vaccination against WN, more efficacious immunization regimens are desired by increasing the antigenic similarity of vaccines to the circulating NY99 strain.

BRIEF SUMMARY OF THE INVENTION

In one aspect, the present invention is directed to a chimeric WN virus derived from at least two WN viral strains, at least one of them being attenuated compared to the highly virulent NY99 strain. The chimeric virus preferably exhibits increased immunogenicity, but low virulence compared to the parent strains.

In a further aspect, the present invention is directed to a (+) RNA chimeric WN virus formed by infectious DNA.

In still another aspect, the present invention is directed to a plasmid DNA encoding a chimeric WN viral genome, which can be amplified in E. coli and easily prepared in large amounts.

In a further aspect, the present invention uses DNA immunization methodology for direct vaccination using the infectious DNA of the present invention, which will provide a stable and safe vaccine for an chimeric (+) RNA virus with increased shelf life due to a higher stability of the purified DNA.

Thus, in one aspect, the invention is directed to a recombinant genetic construct, adapted to encode a live full-length WN viral genome of a live WN virus comprising a nucleic acid region encoding structural proteins of a first WN virus and a nucleic acid region encoding non-structural proteins of a second WN virus, wherein the second WN virus is a different virus from the first WN virus.

In another aspect, the invention is directed to a recombinant chimeric genetic construct wherein the first WN virus and the second WN virus are formed from strains NY99 and WN1415.

In another aspect, the invention is directed to a recombinant chimeric genetic construct wherein a first nucleic acid region encodes the premembrane (prM) and envelop (E) proteins from the NY99 strain and a second nucleic acid region encodes the non-structural proteins NS1, NS2A, NS2B, NS3, NS4A, NS4B and NS5 proteins from the WN1415 virus.

In another aspect, the invention is directed to a recombinant chimeric genetic construct wherein a first nucleic acid region encodes the premembrane (prM), envelope (E), and capsid (C) proteins from the NY99 virus and second nucleic acid region encodes the non-structural proteins NS1, NS2A, NS2B, NS3, NS4A, NS4B and NS5 proteins from the WN1415 virus.

In another aspect, the invention is directed to a recombinant chimeric genetic construct wherein a first nucleic acid region encodes the premembrane (prM), envelope (E), and capsid (C) proteins from the WN1415 virus and the second nucleic acid region encodes the non-structural proteins NS1, NS2A, NS2B, NS3, NS4A, NS4B and NS5 proteins from the NY99 virus.

In a further aspect, a recombinant chimeric genetic construct of the present invention includes a nucleic acid region encoding for a structural protein that includes an E protein that is not glycosylated or contains a mutation, such as SYST at the NYST site.

In still a further aspect, the recombinant chimeric genetic construct of the present invention includes at least one open reading frame interrupting intron downstream from the first occurrence of AUG in the cluster of in-frame AUG codons occurring at the end of the E gene.

In yet another aspect, the recombinant genetic construct of the present invention includes at least one open reading frame interrupting intron in the area encompassing the end of the NS1 gene and beginning of the NS2A gene.

In still another aspect, the recombinant chimeric genetic construct of the present invention is expressed in a vector, such as a plasmid under the control of a eukaryotic promoter (e.g. a CMV promoter).

In still another aspect, the present invention is directed to a host cell stably or transiently transfected the recombinant genetic constructs of the present invention.

In a further aspect, the present invention is directed to a progeny infectious WN virus produced by the cells transfected with the recombinant genetic constructs of the present invention.

The present invention is also directed to an immunogenic composition against WN virus comprising a therapeutically effective amount of the recombinant chimeric genetic constructs a pharmaceutically acceptable carrier.

Additional aspects of the invention, together with the advantages and novel features appurtenant thereto, will be set forth in part in the description that follows, and in part will become apparent to those skilled in the art upon examination of the following, or may be learned from the practice of the invention. The objects and advantages of the invention may be realized and attained by means of the instrumentalities and combinations particularly pointed out in the appended claims.

BRIEF DESCRIPTION OF THE DRAWINGS

FIG. 1 is a schematic drawing of WN956 infectious DNA pCMVWN956. Abbreviations: WN 956 genome cDNA—a cDNA copy of the complete West Nile virus strain 956D117B3 genome (10962 nucleotides in length); δ—hepatitis δ ribozyme sequence (83 nucleotides in length); BG—bovine growth hormone transcription termination and polyadenylation signal sequence (probably around 100 nucleotides in length); CMV—cytomegalovirus promoter/enhancer sequence; bla—ampicillin resistance gene; ori—pBR322 replication origin. Individual elements are not drawn to scale.

FIG. 2 is a schematic drawing of WN NY99 infectious DNA pCMVNY99. Abbreviations: WN NY99 genome cDNA—a cDNA copy of the complete West Nile virus strain NY99 genome (11029 nucleotides in length; not including introns); δ—hepatitis δ ribozyme sequence; BG—bovine growth hormone transcription termination and polyadenylation signal sequence; CMV—cytomegalovirus promoter/enhancer sequence; bla—ampicillin resistance gene; ori—pBR322 replication origin; i2383 and i3472—a 132 bp intron sequence inserted at pos. 2383 and 3472 of the NY99 genome, respectively. Individual elements are not drawn to scale.

FIG. 3 is a schematic of the parent and chimeric infectious DNA constructs of the present invention. The representation of the WN virus genome with genes of recognized virus-specific proteins (Lindenbach and Rice, 2001) is shown on the top. Approximate locations of the introns present in particular constructs are marked by a filled arrowhead, and genome positions of intron insertions are shown below the schematic. For clarity, the schematic is not drawn to scale.

FIG. 4 shows an example of the WN virus recovery from the WN infectious DNA pCMVNY99 construct of the present invention. Evidence for other constructs in similar. WN antigens in transfected cells were visualized by indirect immunofluorescence with WN-specific hyperimmune ascites fluid ("HMAF") and anti-mouse IgG-fluorescein conjugate. Vero cells at 24 hours (left panel) and 40 hours (right panel) after transfection with pCMVNY99 and Lipofectamine 2000 (Invitrogen) are shown.

FIGS. 6A and 6B illustrates the growth characteristics of parent and chimeric viruses. Vero cells were infected at a MOI of 1, and viral progeny was harvested at specified time intervals and titers were determined. The graphs show the amount of: (I) $NY99_{CME}$ virus recovered from pCMV[$CprME_{NY99}$]WN956, (2) $NY99_{ME}$ virus recovered from pCMV[$prME_{NY99}$]WN956, (3) $NY99_{REC}$ virus recovered from pCMVNY99, (4) WN1415 virus recovered from pCMVWN956, and (5) $WN956_{CME}$ virus recovered from (pCMV[$CprME_{WN956}$]NY99. Parent strain NY99 (isolate 385-99), shown in FIG. 4A, and $NY99_{REC}$, shown in FIG. 4B, had essentially the same growth properties.

FIG. 7 shows the cytopathic properties and plaque morphology of the parent and recovered viruses of the present invention. Confluent monolayers of Vero cells were infected with serial 10-fold dilutions of specified viruses and incubated under 1% methylcellulose for five days. Selected wells were either fixed in 10% formalin and stained with methyl violet (upper panel) or fixed in methanol-acetic acid at −20° C. and immunostained with WN-specific HMAF followed by a peroxidase conjugate and the DAB substrate (lower panel). Visualized foci were photographed in visible light.

DETAILED DESCRIPTION OF PREFERRED EMBODIMENT

Figure 5:
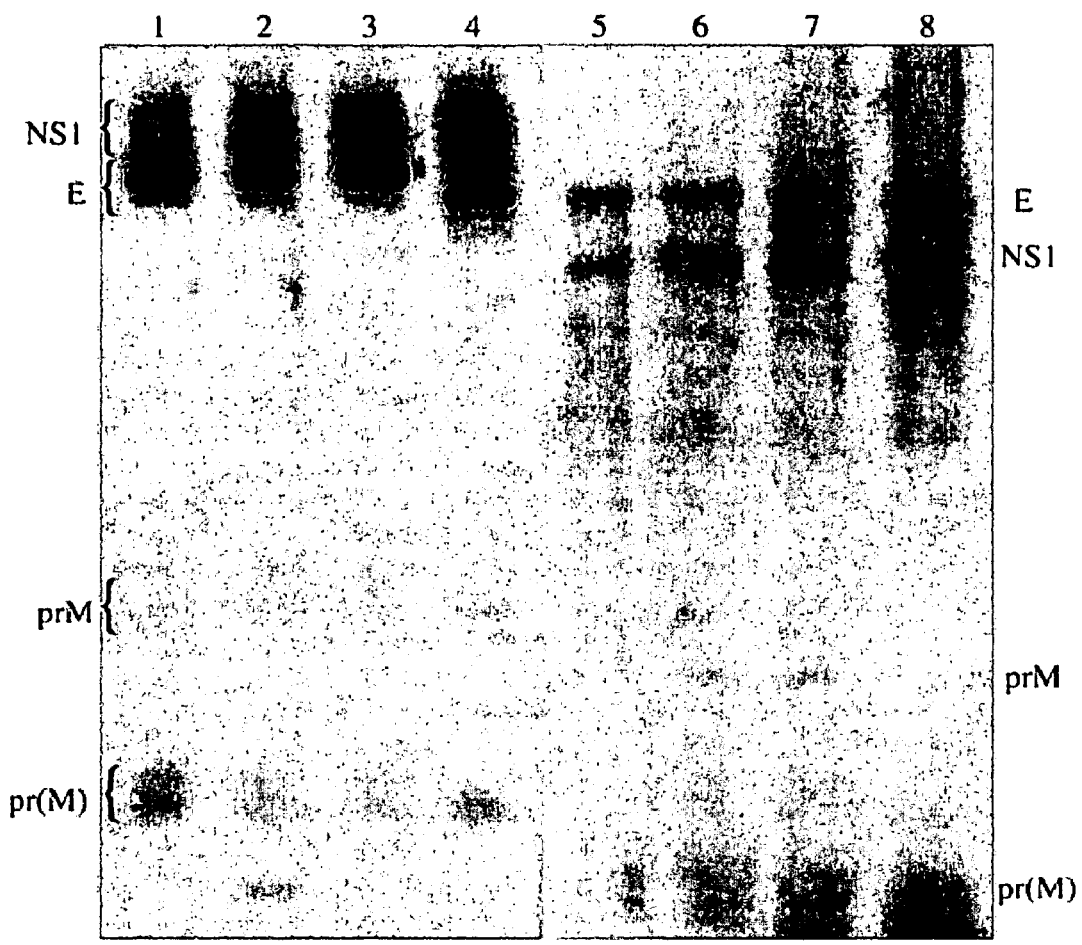
FIG. 5 shows the PAGE analysis of proteins specified by parent and chimeric viruses. [$^{35}$S]-labeled WN-specific proteins were recovered by immunoprecipitation (left panel) from media 24 hours after infection of Vero cells with specified viruses used at multiplicity of infection ("MOI") of 10. Proteins were resolved in 10% polyacrylamide gel under detaturing conditions (SDS-PAGE) and visualized by autoradiography of dried gels. The same samples after deglycosylation with PNGase F are shown on the right panel in Lanes 5-8. Lanes 1 and 5 show the NY99 parent strain. Lanes 2 and 6 show NY99$_{CME}$ recovered from pCMV[CprME$_{NY99}$] WN956. Lanes 3 and 7 show NY99$_{ME}$ recovered from pCMV [prME$_{NY99}$]WN956. Lanes 4 and 8 show WN1415 parent virus recovered as described above from pSP6WN. The WN glycoproteins prM, E, NS1, and pr(M) are identified on the left and right of the audiograph. The label pr(M) designates the glycosylated amino terminal part of prM that is cleaved during virus maturation and is secreted from infected cells.

The present invention is directed to a live attenuated chimeric WN virus and an infectious DNA capable of producing a live attenuated chimeric WN virus. That is, in one aspect of the present invention, the live attenuated virus is produced in vivo using an "infectious DNA" approach. The present invention also relates to a recombinant construct and pharmaceutical composition for eliciting an immune response or a protective immunity against pathogenic WN viruses, including the highly pathogenic NY99 virus strain. According to a related aspect, the present invention relates to a vaccine for preventing and/or treating a WN virus associated disease.

As used herein, the term "treating" refers to a process by which the symptoms of a WN viral replication or associated disease are inhibited, ameliorated, or completely eliminated. As used herein, the term "preventing" refers to a process by which a WN viral replication or associated disease is obstructed or delayed.

The terms "peptide," "oligopeptide," "polypeptide," "polyprotein," and "protein," are used interchangeably herein, and refer to a polymeric form of amino acids of any length, which can include coded and non-coded amino acids, chemically or biochemically modified or derivatized amino acids, and polypeptides having modified peptide backbones.

The term "recombinant," as used herein, means that a particular DNA sequence is the product of various combinations of cloning, restriction, and/or ligation steps resulting in a construct having a structural coding sequence distinguishable from homologous sequences found in natural systems. Generally, DNA sequences encoding the structural coding sequence can be assembled from cDNA fragments and short oligonucleotide linkers, or from a series of oligonucleotides, to provide a synthetic gene that is capable of being expressed in a recombinant transcriptional unit. Such sequences can be provided in the form of an open reading frame uninterrupted by internal nontranslated sequences, or introns, which are typically present in eukaryotic genes. Conversely, for stabilization purposes such sequences can be provided in the form of an open reading frame interrupted by insertion of artificial non-translated sequences, or introns, which naturally are not present in viral genes. Genomic DNA comprising the relevant sequences could also be used. Sequences of non-translated DNA, other than introns, may also be present 5' or 3' from the open reading frame, where such sequences do not interfere with manipulation or expression of the coding regions. Thus, for example, the term "recombinant" polynucleotide or nucleic acid refers to one which is not naturally occurring, or is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

The term "construct" generally refers to recombinant nucleic acid, generally recombinant DNA, that has been generated for the purpose of the expression of a specific nucleotide sequence(s), or is to be used in the construction of other recombinant nucleotide sequences.

Similarly, the terms "recombinant polypeptide" or "recombinant polyprotein" refers to a polypeptide or polyprotein that is not naturally occurring, or is made by the artificial combination of two otherwise separated segments of amino acid sequences. This artificial combination may be accomplished by standard techniques of recombinant DNA technology, such as described above, i.e., a recombinant polypeptide or recombinant polyprotein may be encoded by a recombinant polynucleotide. Thus, a recombinant polypeptide or recombinant polyprotein is an amino acid sequence encoded by all or a portion of a recombinant polynucleotide.

The term "immunologically active" or "immunogenic" refers to the capability of the natural, recombinant, or synthetic virus or peptide, or the natural, recombinant, or synthetic DNA encoding such virus or peptide, to induce a specific humoral and/or cellular immune response upon inoculation in a mammal.

Thus, the term "immune response" refers to a T-cell response or increased serum levels of antibodies to an antigen, or to the presence of neutralizing antibodies to an antigen, such as a WN polypeptide.

The term "protection" or "protective immunity" refers herein to the ability of the serum antibodies or T-cell response induced during immunization to protect (partially or totally) against disease or death caused by the WN virus.

The term "subject" or "patient" of the present invention is preferably a bird, e.g. such as chickens, crows, hawks, parrots, geese, flamingos, etc. or mammal, e.g., such as mice, cows, pigs, horses, chickens, cats, dogs, etc., and is preferably a human.

The term "therapeutically effective dose" or "therapeutically effective amount" means a dose or amount that produces the desired effect for which it is administered. The exact dose will depend on the purpose of the treatment, and will be ascertainable by one skilled in the art using known techniques.

The term "pharmaceutically acceptable" means approved by a regulatory agency of the federal or a state government or listed in the U.S. Pharmacopeia or other generally recognized pharmacopeia for use in animals, and more particularly, in humans.

The term "carrier" refers to a diluent, adjuvant, excipient, or vehicle with which the attenuated live recombinant virus or infectious DNA is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

Thus, as used herein, the term "pharmaceutically acceptable carrier" means, but is not limited to, a vehicle for containing the DNA constructs or the attenuated live recombinant virus of the present invention that can be injected into a mammalian host without adverse effects. Suitable pharmaceutically acceptable carriers known in the art include, but are not limited to, gold particles, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

In the present invention, as discussed more fully below, a WN infectious DNA construct comprised of a chimeric genome of NY99 and WN956 viruses was placed under transcriptional control of an eukaryotic promoter and inserted into a derivative of the *E. Coli* cloning vector pBR322 plasmid. A CMV promoter from the pCIneo plasmid was used to drive transcription.

It will be appreciated to those skilled in the art that the infectious DNA of the present invention may be formed using any suitable vector. In general, a vector is a nucleic acid molecule (typically DNA or RNA) that serves to transfer a passenger nucleic acid sequence (i.e., DNA or RNA) into a host cell. Three common types of vectors include plasmids, phages and viruses. Preferably, the vector is a plasmid. That is, the infectious DNA vaccines of the present invention are comprised of DNA that is produced as a plasmid that can be introduced into animal tissue and therein is expressed by animal cells to produce a messenger ribonucleic acid (mRNA) molecule of the size of the WN genome, which is translated to produce a viral polyprotein, that is processed by cellular machinery to provide a full set of WN proteins that are capable to initiate replication of the above primary RNA transcript and thus initiate the virus replication cycle in animal tissue into which the above DNA plasmid was introduced.

Suitable and exemplary plasmid vectors that have been used in conventional DNA vaccines include, but are not limited to pBR322 (ATCC#31344); pUC19 (ATCC#37254); pcDNA3.1 (Invitrogen, Carlsbad Calif. 92008; Cat. NO. V385-20; DNA sequence available at http://www.invitrogen.com/vectordata/index.html); pNGVL (National Gene Vector Laboratory, University of Michigan, Mich.); p414cyc (ATCC#87380), p414GALS (ATCC#87344), pBAD18 (ATCC#87393), pBLCAT5 (ATCC#77412), pBluescriptI-IKS, (ATCC#87047), pBSL130 (ATCC#87145), pCM182 (ATCC#87656), pCMVtkLUC (ATCC#87633), pECV25 (ATCC#77187), pGEM-7zf (ATCC#87048), pGEX-KN (ATCC#77332), pJC20 (ATCC#87113, pUB110 (ATCC#37015), pUB18 (ATCC#37253).

As discussed herein, the infectious DNA of the present invention is also under the control of a suitable promoter. For eukaryotic expression, suitable promoters include the cytomegalovirus ("CMV") early promoter, or alternatively the Rous sarcoma virus ("RSV") LTR promoter, and the SV40 promoter.

The amount of the recombinant constructs present in the immunogenic compositions, of the present invention are preferably a therapeutically effective amount as defined above. A therapeutically effective amount of plasmid is generally that amount necessary so that the nucleotide sequence coding for the WN polypeptide performs its immunological role without causing overly negative effects in the host to which the composition is administered. The exact amount of plasmid to be used and the composition/vaccine to be administered will vary according to factors such as the strength of the transcriptional promoters used, the type of condition being treated, the mode of administration, as well as the other ingredients in the composition. Preferably, the composition or the vaccine formulation is composed of from about 10 ng to about 1 µg of plasmid. It is important to note that conventional non-replicating DNA vaccines usually require larger amounts of DNA (typically 10 to 100 µg) of plasmid. Thus, in the present invention, the therapeutically effective amount is substantially reduced compared to that of non-infectious DNA vaccines.

The immunogenicity of the DNA vaccine and pharmaceutical compositions of the present invention can also be modified by formulating with a pharmaceutically acceptable adjuvants or immunostimulants, such as alpha-interferon, beta-interferon, gamma-interferon, granulocyte macrophage colony stimulator factor ("GM-CSF"), macrophage colony stimulator factor ("M-CSF"), interleukin 2 ("IL-2"), interleukin 12 ("IL-12"), and CpG oligonucleotides. For preparing such compositions, methods well known in the art may be used.

Subcutaneous injection, intradermal introduction, impression through the skin, and other modes of administration such as intraperitoneal, intravenous, oral, or inhalation delivery are also suitable. For example, vectors containing the infectious DNA of the present invention can be introduced into the desired host by methods known in the art, for example, transfection, electroporation, microinjection, microparticles, microcapsules, transduction, cell fusion, DEAE dextran, calcium phosphate precipitation, lipofection (lyposome fusion), use of a gene gun (particle bombardment), or a DNA vector transporter (see, e.g., Wu et al., 1992, J. Biol. Chem. 267:963-967; Wu and Wu, 1988, J. Biol. Chem. 263:14621-14624; Hartmut et al., Canadian Patent Application No. 2,012,311, filed Mar. 15, 1990).

Administration may be single or multiple (i.e. single-dose or including a booster). Such administration may be alone or in combination with other active therapeutic agents against WN virus.

In the following examples, the DNA manipulations were performed using the standard procedures (Sambrook and Russell, 2001) with commercially available enzymes in conditions recommended by manufacturers. Total RNA from infected cells was isolated using the RNeasy Mini kit (Qiagen, Valencia, Calif.). PCR and RT-PCR amplification was performed using high fidelity KOD polymerase (Novagen, Madison, Wis.). A set of primers for amplification and sequencing of WN viral isolate 385-99 cDNA fragments was designed on the basis of the WN viral isolate 382-99 sequence (GenBank #AF196835). Sequencing of cDNA fragments and plasmids was done using ABI310 Genetic Analyzer (Perkin-Elmer) with the manufacturer's kits and protocols. Throughout the examples, NIH Guidelines for Research involving Recombinant DNA Molecules were followed. *E. coli* strain HB101 was used for cloning and maintenance of recombinant constructs. Vero cells (ATCC CRL-1586) were maintained at 37° C. in a humidified atmosphere containing 5% $CO_2$ in Dulbecco's modified Eagle medium (DMEM) supplemented with 5% fetal calf serum (FCS; Hyclone, Logan, Utah) and 1× antibiotic—antimycotic mixture (Invitrogen, Carlsbad, Calif.).

EXAMPLE 1

Construction of pCMVWN956

Isolate WN956D117B3 (earlier also referred to as WN-Nigeria or WN-Wengler (Berthet et al., 1997; Lanciotti et al., 1999)) is a descendant of the WN virus prototype B956 (Smithburn et al., 1940), and is one of the first flaviviruses for which the complete nucleotide sequence has been determined (Castle et al., 1986; Castle et al., 1985; Wengler et al., 1985; GenBank #M12294). Archival RNA isolated from WN956D117B3 was used to rescue the virus, and to prepare the cDNA fragments which were used to assemble the WN infectious clone designated as pSP6WN/Xba, and describe in co-pending Patent application Ser. No. 11/065,783, which is incorporated by reference. For simplicity, the pSP6WN/Xba infectious clone shall be referred to herein as pSP6WN956 to better reflect its relationship to the parent virus strain WN956D117B3.

To simplify handling, the infectious clone pSP6WN956 was converted to an infectious DNA format by engineering a CMV promoter transcription start at the beginning of the WN genome cDNA and a ribozyme-transcription terminator cassette at the end of the WN genome cDNA. A 738 bp fragment containing the CMV promoter/enhancer including its transcription start was amplified from the pCIneo plasmid (positions 6-743 on the pCIneo map; Promega, Madison, Wis.); a Cla I site was included into the direct primer. The CMV transcription start was engineered by overlapping PCR to the beginning of the WN genome cDNA (transcripts lacking the first nucleotide of the WN genome are not infectious) and the resulting joint CMV-5'UTR was used as Cla I -Bgl II fragment to replace the corresponding SP6-5'UTR Cla I -Bgl II fragment in pSP6WN956. The optimal configuration was selected by introducing 0, 1 or 2 thymidine spacers at the junction (i.e. . . . SEQ ID NO: 1 GAACCGAGTAGTT CG. . . , SEQ ID NO: 2. . . GAACCGTAGTAGT. . . , or SEQ ID NO: 3. . . GAACCGTTAGTAGTTCG. . . , where the promoter sequence adjacent to the transcription start is underlined and the beginning of WN genome cDNA is shown in bold) with subsequent evaluation of the specific infectivity of the final constructs. The highest specific infectivity was obtained with one thymidine spacer and this configuration was subsequently used in the design of all other constructs, including the pCMVNY99 plasmid discussed in Example 2 and the recombinant plasmids discussed in Example 3.

Figures 1, 2:
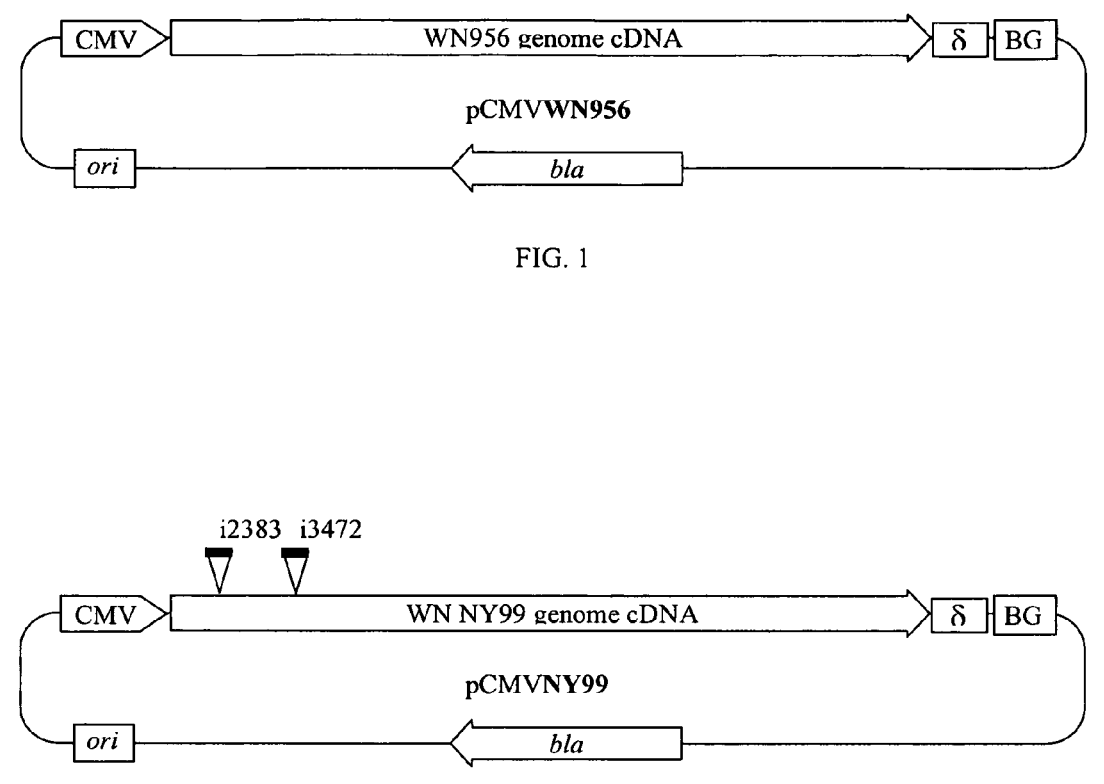

A 347 bp fragment containing the hepatitis δ ribozyme followed by the bovine growth hormone transcription termination and polyadenylation signal (the δ BG cassette, FIG. 1) was assembled by joining the δ ribozyme containing the 82 bp Sma I-Sac fragment from the plasmid p2.0 (Pattnaik et al., 1992) to a BG containing 265 bp Sac I-Pvu II fragment from the plasmid pcDNA3 (pos. 1021-1286 on the pcDNA3 map; Invitrogen, San Diego, Calif.). Insertion of the resulting blunt-ended joint fragment at the end of the WN genome cDNA was done as described earlier (Yamshchikov et. al., 2001 a; Yamshchikov et. al., 2001b). Such a cleavage site of the ribozyme is precisely engineered to the 3'-end of the WN genome (which is 10,956 nucleotides in length). The ribozyme sequence cleaves itself off leaving no additional nucleotides at the 3'-end of the WN genome RNA. The BG sequence causes termination of transcription. The resulting construct designated pCMVWN956 was characterized by complete sequencing of the WN genome cDNA insert.

EXAMPLE 2

Construction of pCMVNY99

In this example, an infectious clone of the WN NY99 strain was assembled using the WN viral isolate 385-99 (Xiao et al., 2001), reported as GenBank #AY842931, which is incorporated by reference. The WN viral isolate 385-99 of the NY99 strain at Vero passage 1 was kindly provided by R. Tesh (Galveston, Tex.) and the working stock ($8.8×10^7$ pfu/ml) was prepared by additional passage in Vero cells. There is one silent A→G substitution at position 630 in the nucleotide sequence of the reported WN viral isolate 385-99 genome (GenBank #AY842931) as compared to the sequence found by the present inventors on the passaged virus, which has been reported (GenBank #DQ211652, which is incorporated by reference).

To construct the infectious DNA plasmid encoding the NY99 strain, a similar Cla I-Bgl II CMV-5'UTR joint fragment was created using WN viral isolate 385-99 cDNA, that was used to assemble a CMV-driven subgenomic replicon construct lacking genes C, prM and E (deletion from positions. 162 to 2352 of the NY99 genome). The functional integrity of this part of the genome was verified by testing the replication competency of RNA produced from this construct as described earlier (Yamshichikov et al., 2001b).

The δBG cassette was engineered at the 3' end of the WN viral isolate 385-99 genome as discussed above.

In attempt to incorporate the omitted structural region, it was found that a sequence at the end of the E gene (positions 1900 to 2150) strongly interferes with downstream sequences resembling a promoter-like element found in the JE genome (Yamshchikov et al., 2001a). Therefore, a similar strategy was used to eliminate this interference. The C-prM-E structural protein gene cassette of WN viral isolate 385-99 was modified by PCR mediated insertion of a 132 bp intron at either position 2210 or 2384, and by an introduced Mfe I site (position 2405). The 132 base pair artificial intron carrying stop codons in three frames was amplified from pCIneo (positions 890-1022 of the pCIneo map. The modified structural gene cassettes were inserted as Bgl II-BspE I fragments into the WN viral isolate 385-99 replicon plasmid replacing the corresponding fragment carrying the deletion.

A marginally stable full-length construct denominated pCMVNY99(i2210)δBG was assembled after insertion of a 132 base pair intron at position 2210 of the 385-99 genome, which produced virus after transfection into Vero cells (results not shown). However, poor growth of *E. coli* harboring the plasmid indicated that the construct remained toxic and the destabilizing effect was not completely eliminated.

An increased stability was observed after relocation of the 132 base pair intron from position 2210 to position 2384 of the 385-99 genome, downstream from a cluster of in-frame AUG codons occurring at the end of the E gene. The complete stabilization was achieved after insertion of a second copy of the intron at position 3472 of the 385-99 genome, because deletion mutagenesis revealed yet another strong destabilizing interference of the above element, with a fragment including the carboxy terminal part of NS1 and the most of the NS2A gene. The presence of two OFR-interrupting introns (i2384 and i3472) was found to be important for the stability of the plasmid in *E. coli*. The construct was not toxic for the bacterial host and could be propagated at high yields. The final construct is denominated pCMVNY99(i2383i3472) δBG or simply pCMVNY99 and is generally shown in FIG. 2.

Twelve non-conservative mutations were identified in the resulting NY99 genome, which presumably accumulated during assembly pCMVNY99. Fragments carrying these mutations were replaced using de novo cDNA and flanking restriction enzyme sites. Except for the two introns and a Mfe I site introduced by silent mutation at the end of E gene at the same position as in the WN956 genome, the nucleotide sequence of viral genome cDNA in pCMVNY99 is authentic to the WN viral isolate 385-99 genome as set forth in GenBank No. #DQ211652.

EXAMPLE 3

Preparation of Chimeric Constructs

Figures 3, 4:
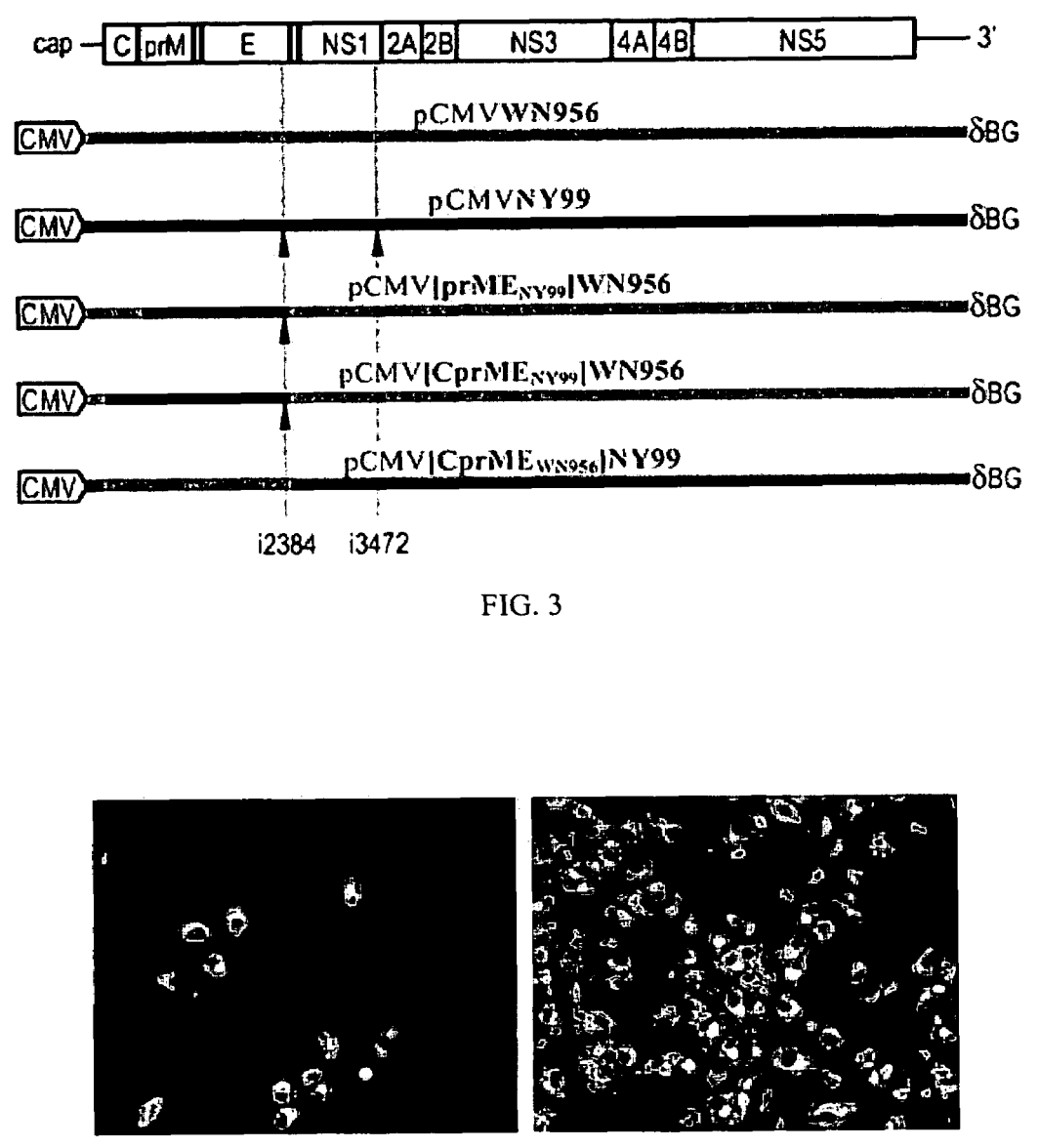

In this example, the pCMVWN956 and pCMVNY99 constructs from Examples 1 and 2 were used to create plasmids carrying reciprocal exchanges of the structural protein genes of two viruses as shown in FIG. 3. Three chimeric constructs were prepared. The pCMV[CprME$_{NY99}$]WN956 chimera carries genes of all NY99 structural proteins (C, prM, and E) instead of those of WN956. In the pCMV[prME$_{NY99}$]WN956 chimera, only the prM-E region of NY99 (not including its prM signal sequence) from position 466 to 2405 was used to replace the corresponding region in the pCMVWN956 construct. The last chimeric construct pCMV[CprME$_{WN956}$]NY99 was created by transferring the Bgl II-Mfe I fragment coding for CprME of WN956 into pCMVNY99.

More specifically, reciprocal exchanges of the C-prM-E genes between pCMVWN956 and pCMVNY99 were done by exchange of the corresponding Bgl II-Mfe I fragments (from position 89, 8 nucleotides upstream from the beginning of NY99 and WN956 ORF, to position 2393 in WN956 and 2405 in NY99 at the amino terminus of the NS1 signal sequence). A fragment including only the prM-E genes of WN viral isolate 385-99 was created by PCR-mediated engineering of the carboxy terminus of the internal prM signal peptide of WN956 (including the signalase cleavage site) to the amino terminus of mature prM of WN viral isolate 385-99 with subsequent transfer of the chimeric C-prM-E cassette as the Bgl II-Mfe I fragment.

Interestingly, the stability of the first two chimeric constructs (pCMV[CprME$_{NY99}$]WN956 and pCMV[prME$_{NY99}$]WN956) depended on the presence of i2384. In both these constructs, the sequence downstream from Mfe I (position 2405) is the same as in pCMVWN956, which is perfectly stable without an intron at the end of the E gene (such as i2384). On the other hand, the latter chimeric construct carrying the E gene of WN956 and the downstream interfering regions from NY99 also does not require an intron at this position. This evidence corroborates the presence of a strong dominant destabilizing element at the end of the NY99 E gene

EXAMPLE 4

Mutagenesis of the Parent and Chimeric Constructs to Eliminate the Glycosylation Site In this example, infectious DNA constructs from prior examples that encode the E protein of the NY99 virus were used to prepare modified constructs that specify the E protein that is not glycosylated. Modified constructs were prepared from pCMVNY99, CMY[CprME$_{NY99}$]WN956 and pCMV [prME$_{NY99}$]WN956 infectious DNA The E protein of NY99 carries a single glycosylation site (Asp-Tyr-Ser-Thr or NYST, position 154-157 in the E protein). Several lines of evidence indicate that highly virulence of NY99 positively correlates with the glycosylation status of its E protein (Beasley et al., 2005; Shirato et al., 2004). We anticipate that elimination of this glycosylation site will reduce virulence of chimeric viruses recovered from modified pCMV[CprME$_{NY99}$]WN956 and pCMV[prME$_{NY99}$]WN956. A virus recovered from modified parent pCMVNY99 would serve as a corresponding reference control.

Elimination of the glycosylation site was accomplished by PCR-mediated mutagenesis or PCR-mediated deletion mutagenesis. Pairs of complementary primers were synthesized for each mutant as follows.

To introduce a single point mutation (NYST→SYST), which would eliminate the glycosylation site without changing the size of E protein, a direct primer NY1414Md (SEQ ID NO: 4 GAG TCG CAC GGA TCC TAC TCC ACA CA) and a reverse primer NY1439mR (SEQ ID NO: 5 TG TGT GGA GTA GGA TCC GTG CGA CTC) that is complementary to NY1414mD, were synthesized. The mutagenized codon introducing the Asn→Ser mutation is shown in bold.

To introduce a deletion encompassing the entire glycosylation site, a direct primer NY1438delD (SEQ ID NO: 6 TCG CAC GGA*CAG GTT GGA GCC ACT CAG GCA) and a reverse primer NY-1425delR (SEQ ID NO: 7 TCC AAC CTG*TCC GTG CGA CTC CAC AGT AGT), which is partially overlapping and complementary to NY1438delD, were synthesized. In the provided sequences, asterisk indicates the position where the NYST-encoding sequence (SEQ ID NO: 8 AAC TAC TCC ACA), which is being deleted, is normally located in the sequence of the E gene.

To introduce a deletion encompassing the entire glycosylation site and introduce adjacent mutations (GNYSTQV→GΔKI) found in the sequence of WN1415 protein E (that carries a deletion of the entire site), a direct primer NY1439delmD (SEQ ID NO: 9 TCG CAC GGA*AAG ATT GGA GCC ACT CAG GCA) and a reverse primer NY1425delmR (SEQ ID NO: 10 TCC AAT CTT*TCC GTG CGA CTC CAC AGT AGT), which is partially overlapping and complementary to NY1439delmD, were synthesized. In the provided sequences, asterisk indicates position where the NYST-encoding sequence (SEQ ID NO: 11 AAC TAC TCC ACA), which is being deleted, is normally located and single nucleotide changes resulting in the Q→K and V→I mutations are underlined.

The above primer pairs were used in combination with primers flanking the Bgl II and Mfe I sites used in assembly of pCMVNY99 and the chimeric constructs as described in previous examples. Fragments carrying the specified mutations and deletion were amplified by two-step PCR using pCMVNY99 as a template, purified by gel-electrophoresis, and used as Bgl II-Mfe I fragments to replace the corresponding Bgl II-Mfe I fragments with the wild type sequence in pCMVNY99, pCMV[CprME$_{NY99}$]WN956 and pCMV [prME$_{NY99}$]WN956.

The final infectious DNA constructs were characterized by sequencing to ensure that all intended mutations are in place and no other mutations were introduced during genetic engineering manipulations. The resulting constructs and corresponding viruses recovered from these constructs were designated using designation of the parent wild type construct or virus with addition of corresponding mutation or deletion. That is, the corresponding constructs originated from pCMV

[prME$_{NY99}$]WN956 are pCMV[prME$_{NY99}$(SYST)]WN956, pCMV[prME$_{NY99}$ (ΔNYST)]WN956, and pCMV[prME$_{NY99}$ (ΔNYSTKI)]WN956, and recovered viruses are NY99$_{ME}$SYST, NY99$_{ME}$ΔNYST, and NY99$_{ME}$ΔNYSTKI

EXAMPLE 5

Recovery of Chimeric and Mutagenized Viruses, Determination of Virus Titers, and Characterization of Viruses in Tissue Culture In this example, the DNA constructs from prior examples were used to recover the corresponding viruses. All of the DNA constructs described above (pCMVWN956, pCMVNY99, CMV[CprME$_{NY99}$]WN956, pCMV[prME$_{NY99}$]WN956, and pCMV[CprME$_{WN956}$]NY99) were infectious in tissue culture, i.e. lipid-mediated direct transfection of Vero, BHK, or mosquito C6/36 cells with either of these plasmids resulted in establishment of a productive infection. Infectious properties of the mutagenized derivatives were confirmed in BHK and Vero cells.

The DNA constructs were also used to obtain virus stocks. Transfection of Vero cells with infectious DNA constructs from Examples 1, 2, and 3 was done using the Lipofectamine 2000 transfection reagent (Invitrogen, Carlsbad, Calif.) according to the manufacturer's protocol. Briefly, a transfection mixture containing 0.8 μg of infectious DNA and 3 μl of the reagent in 100 μl of Opti-MEM (Invitrogen) was added to a 70-80% confluent Vero cell monolayer in a 12-well plate cluster. After 6-8 hours incubation under the normal growth conditions, the transfection medium was replaced with the fresh growth medium and incubation was continued for additional 2-3 days to allow sufficient accumulation of the passage 1 progeny. Working stocks of passage 2 viruses were prepared by infecting Vero with the passage 1 progeny at MOI of 0.1 and harvesting the progeny from the medium 4-5 days post infection. Titers of viral stocks at passage 2 prepared in Vero cells were $1.4 \times 10^8$ (NY99$_{CME}$), $5.7 \times 10^7$ (NY99$_{ME}$), and $3.1 \times 10^7$ (WN956$_{CME}$) pfu/ml, $8.8 \times 10^7$ (NY99$_{REC}$), $2.6 \times 10^7$ (WN1415) pfu/ml, $8 \times 10^6$ (NY99$_{ME}$SYST), $3 \times 10^4$ (NY99$_{ME}$ΔNYST), and $6 \times 10^4$ (NY99$_{ME}$ΔNYSTKI) pfu/ml.

Total RNA isolated from the infected cells (remaining after the passage 2 viral stock was harvested) was used for RT-PCR amplification of overlapping cDNA fragments, which were gel-purified and sequenced as above. For indirect immunofluorescence, cells were seeded on glass coverslips in 24-well plate clusters and half of the DNA and transfection reagent was used under the same conditions. Cells fixed with acidic methanol were processed for WN-specific indirect immunofluorescence as described earlier (Yamshchikov et al., 2001b). Viral proteins were labeled with [$_{35}$S]Met about 24 hours after infection of Vero cells with specified viruses at MOI=10. The labeling, immunoprecipitation, deglycosylation with PNGase F, and PAGE analysis was done as described earlier (Yamshchikov and Compans, 1993; Yamshchikov and Compans, 1995; Yamshchikov et al., 1997). Virus titers were determined by 96-well microassay (Yamshchikov et al., 2004). The specific infectivities of the DNA constructs, virus cytopathic properties and plaque morphology were analyzed as described (Yamshchikov et al., 2004; Yamshchikov et al., 2001a; Yamshchikov et al., 2001b). Briefly, transfected or infected Vero cell monolayers were incubated in the growth medium containing 1% methylcellulose, washed, fixed and either stained with methyl violet or immunostained with WN-specific hyperimmune ascites fluid (HMAF) and the peroxidase-DAB procedure.

All of the constructs described above were infectious in tissue culture. As an example shown in FIG. 4, the foci of virus multiplication were easily detectable by indirect immunofluorescence 24 hours after transfection with pCMVNY99, and by 40 hours after transfection the entire Vero monolayer was infected. No obvious differences in the spread of infection were discernible between chimeric and parent viruses using this assay. The specific infectivity of iDNA was in the range $3\text{-}8 \times 10^6$ pfu/μg DNA in Vero cells.

The viruses recovered from the recombinant DNA constructs were designated as follows: (1) NY99$_{REC}$ recovered from pCMVNY99; (2) NY99$_{CME}$ recovered from pCMV [CprME$_{NY99}$]WN956, (3) NY99$_{ME}$ recovered from pCMV [prME$_{NY99}$]WN956, and (4) WN956$_{CME}$ recovered from pCMV[CprME$_{WN956}$]NY99. Genomes of all virus isolates were completely sequenced at Vero passage 2 and demonstrated the expected nucleotide sequences constructed on the basis of WN956 (GenBank #M12294) and WN viral isolate 385-99 (GenBank #DQ211652) genome sequences. That is, NY99$_{REC}$ recovered from pCMVNY99 was genetically (with the exception of the Mfe I site at position 2405) and phenotypically identical to the parent NY99 strain isolate 385-99.

The C proteins of WN956 and NY99 differ in three amino acids (Asn$_{11}$→Ser, Gly$_{24}$→Val, and Thr$_{100}$→Ser), but the prM signal sequence is more divergent. In addition, the prM signal sequence in NY99 is shorter by three amino acids than in WN956 due to the presence of Lys$_{108}$. In NY99$_{ME}$, to minimize possible negative effects of such divergence, C and the prM signal peptide of WN956 were engineered to the prM and E of NY99. Since all constructs produced viable chimeric viruses, this appeared not to be an important issue. All recovered viruses were completely characterized by sequencing and were found to be genetically stable, at least up to passage 2, at which the biological properties were investigated.

The glycosylation status of glycoproteins specified by the parent and chimeric viruses was verified by immunoprecipitation, deglycosylation with PNGase F and SDS-PAGE. The prM and NS1 proteins of both NY99 and WN956 each carry glycosylation sites, and all are glycosylated as shown in FIG. 5 (lanes 1, 5 and 4, 8, respectively). While the E protein of NY99 is also glycosylated at the NYST site (position 154-157 in the E protein), the E protein of WN1415 (as well as its parent WN956 and its ancestor B956) carries a deletion of the entire 4 amino acid site. Accordingly, the E protein of WN1415 is not glycosylated (FIG. 5, lanes 4, 8). In contrast, cells infected with either NY99 or both chimeric NY99$_{CME}$ and NY99$_{ME}$ produce glycosylated E (FIG. 5, lanes 1-3 and 5-7, respectively). WN HMAF used for immunoprecipitation was prepared against WN956 (Yamshchikov et al., 1997; Yamshchikov et al., 2001b). It appears less efficient in immunoprecipitation of secreted NS1 of NY99, which is represented by a diffuse band due to the heterogeneity of the oligosaccharide moiety (FIG. 5, lane 1) and is better revealed after deglycosylation (FIG. 5, lane 5). Both chimeric viruses specify NS1 of WN956, which is efficiently recovered as for WN1415 (FIG. 5, lanes 3-4 and 6-8, respectively)

Figure 6A:
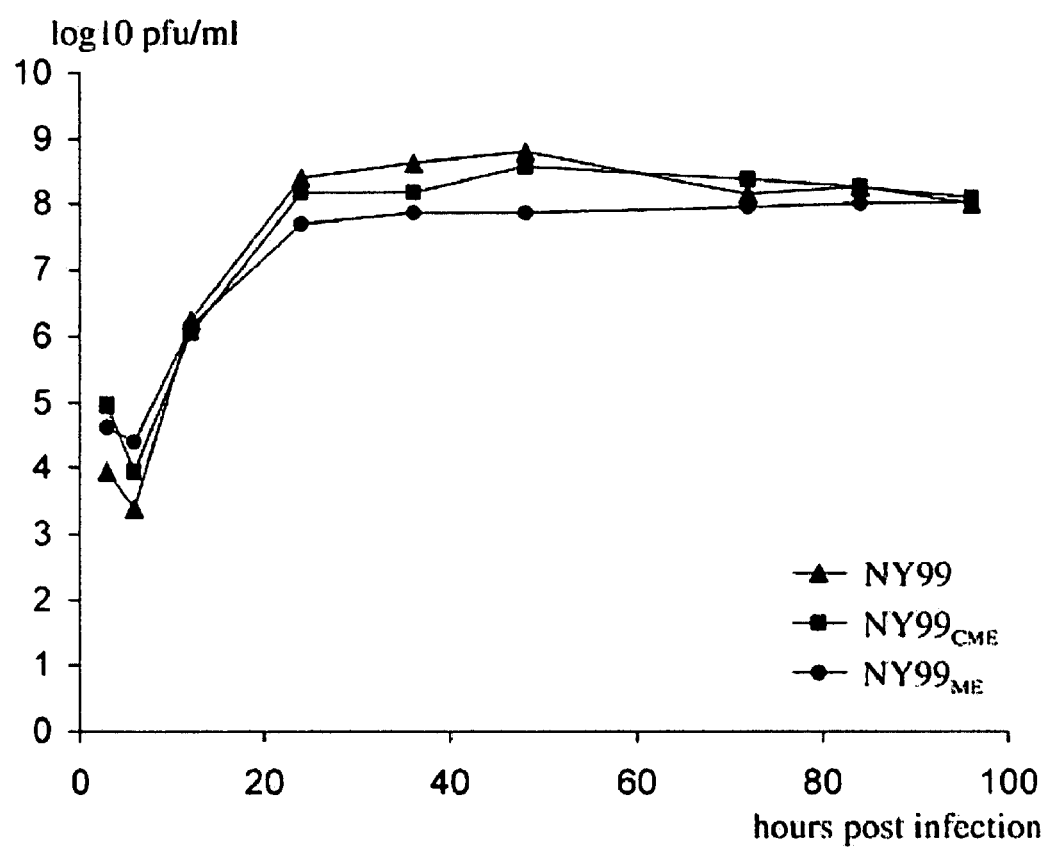
Figures 6B, 7:
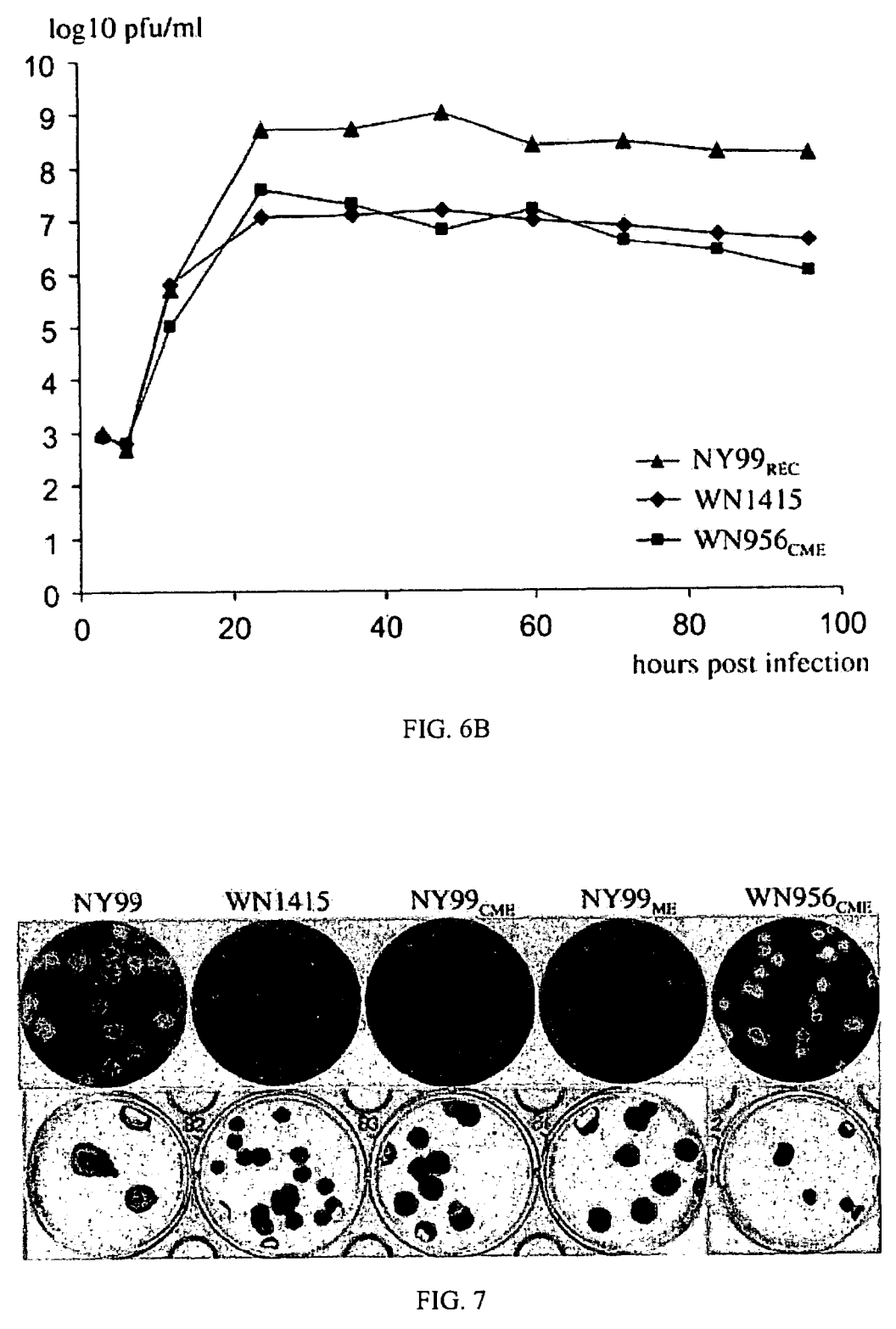

As shown in FIG. 6, the growth characteristics of the parent (NY99) and the recovered recombinant viruses (NY99$_{REC}$, NY99$_{CME}$, and NY99$_{ME}$), such as the growth rate and the efficiency of viral spread indicated by the plague size, were examined in Vero cells. As expected, parent strain NY99 and NY99$_{REC}$ recovered from the parent infectious DNA construct pCMVNY99 demonstrated the essentially similar growth curves (FIGS. 6A and 6B). As shown in FIG. 6A, NY99$_{CME}$ accumulated at the rate essentially similar to NY99, while NY99$_{ME}$ that inherited C and the prM signal peptide from WN956 demonstrated a somewhat slower accumulation.

As shown in FIG. 6B, the growth curve of the WN956$_{CME}$ chimera that carries the structural protein genes of WN956 and the rest of the genome from NY99 was found to be very similar to WN1415 with peak titers lower than observed for NY99$_{REC}$ by 10 to 100 fold.

The prominent phenotypic difference between parent NY99 strain and WN1415 (recovered from pCMVWN956) is the high cytopathic effect in Vero cells that is characteristic for the former and is absent for the latter (FIG. 7). Surprisingly, both NY99$_{CME}$ and NY99$_{ME}$ carrying the structural protein genes of NY99 retained the phenotype of WN1415, which does not form distinctive plaques in Vero cells (FIG. 7, the upper panel). Foci of virus multiplication was barely visible on fixed and stained monolayers as pale areas without discernible cell destruction. Immunohistochemical staining of fixed cells showed that NY99$_{CME}$ and NY99$_{ME}$ actually form larger foci, which is indicative of a higher efficiency of viral spread, resembling NY99 more than WN1415 (FIG. 7, the lower panel). This phenotypic marker agrees with the higher accumulation rates of both NY99$_{CME}$ and NY99$_{ME}$ demonstrated above, which is characteristic for NY99. In contrast, WN956$_{CME}$ carrying the structural protein genes of WN956 in the NY99 genome displayed an essentially reversed phenotype. It demonstrates a clearly cytopathic phenotype of NY99 (FIG. 7, the upper panel). However, the growth rate (FIG. 6B) and the plaque/foci size of WN956$_{CME}$ (FIG. 7, the lower panel) resembles WN11415.

The differences in the growth rate correlate with the efficiency of virus spread judged by the size of virus multiplication foci formed under semisolid overlays and visualized by immunohistochemical staining as antigenpositive cells. The combined evidence indicates that both the higher growth rate and the higher efficiency of viral spread characteristic for the NY99 strain are determined by the properties of its structural proteins. In contrast, determinants that are responsible for the cytopathic effect of NY99 (or lack thereof for WN1415) were found to be associated with the non-structural proteins. This conclusion is strongly supported by the essentially reversed phenotype of WN956$_{CME}$ that carries the structural protein genes of WN956 in the NY99 genome.

To date, the genetic determinants responsible for the cytopathicity of flaviviruses or mechanisms by which the cytopathic effect is induced are not clearly defined. For WN viruses, either necrosis or induction of apoptotic cell death have been observed depending on the virus dose (Chu and Ng, 2003). A number of evidence implicated NS3 in induction of apoptosis by dengue and WN viruses (Duarte dos Santos et al., 2000; Ramanathan et al., 2005). Although three amino acid and 26 amino acid differences distinguish NS2B and NS3 of WN956 and NY99, all these are shared by noncytopathic WN 1415 and its cytopathic ancestor B956 (Yamshchikov et al., 2004). This indicates that neither the NS2B-NS3 protease or NS3 alone are not responsible for the observed differences in cytopathicity. On the other hand, selected single mutations at position 15 in the amino terminus of pestivirus NS4B were found critical for the emergence of non-cytopathic isolates (Qu et al., 2001). While the functional role of WN NS4B may somewhat differ from that of pestivirus NS4B, their similar genomic location (Lindenbach and Rice, 2001) suggests their involvement in the function of the viral replicase complex. Interestingly, NS4B of WN1415 includes two unique mutations ($S_{13} \rightarrow G$, $A_{100} \rightarrow V$) that distinguish it from both NY99 and B956 NS4B, with the first of these found in a similar to pestivirus NS4B location.

Virulence of many of flaviviruses, which in the mouse model is exhibited as neuroinvasiveness and/or neurovirulence, has been associated with determinants in the envelope protein (Cecilia and Gould, 1991; Chambers et al., 1999; Gualano et al., 1998; Hasegawa et al., 992; Holzmann et al., 1990; Holzmann et al., 1997; Jiang et al., 1993; McMinn, 1997; Pletnev t al., 1992; Pletnev et al., 1993). It has been shown that neuroinvasiveness and thus the highly virulent phenotype of NY99 and other lineage 1 strains at least in part is determined by the glycosylation status of the E protein (Beasley et al., 2005; Shirato et al., 2004). A few highly virulent lineage 2 strains have also been identified (Beasley et al., 2002) with the majority of them carrying glycosylated E protein. Accordingly, it was expected that transfer of the NY99 structural protein genes along with the expected increased growth rate would result in transfer of the NY99 highly virulent phenotype. However this was not found to be the case, although a certain increase in virulence was observed based on LD$_{50}$ values of attenuated WN1415 and both chimeric NY99$_{CME}$ and NY99$_{ME}$.

WN1415, WN956 and their ancestor B956, which displayed various levels of attenuation (Yamshchikov et al., 2004), carry a deletion of four amino acids that compose the E$_{154-157}$ glycosylation locus (NYST in the majority of lineage 1 viruses). In this example, replacement of the authentic E gene with the gene of glycosylated E from NY99 produced NY99$_{CME}$ and NY99$_{ME}$ with the increased virulence. This does not contradict the existing evidence supporting the importance of E glycosylation for expression of the virulent phenotype. However, transfer of the gene coding for non-glycosylated E from WN956 into the NY99 genome produced the WN956$_{CME}$ chimeric virus with essentially the same virulence in mice as NY99 despite its overall poorer growth characteristics in tissue culture. The combined evidence suggests that the determinants of the high virulence of NY99, as well as the genetic basis of WN1415 attenuation, are found in the nonstructural protein region.

EXAMPLE 6

Virulence and Pathogenicity of Recovered Viruses

In this example, the peripheral virulence of the parent and chimeric viruses was assessed in 4-week old outbred Swiss Webster mice purchased from Charles River (Wilmington, Mass.), which were infected intramuscularly with serial 10-fold dilutions of viral stocks. The mice were maintained in a BL3 facility according to the NIH guidelines, and used in IACUC-approved protocols. The mice were infected into the tibialis anterior muscle (i.m.) with virus dilutions prepared in PBS plus 0.2% normal mouse serum and observed for three weeks. Mice that developed the encephalitic syndrome such as paralysis were euthanized and counted as lethal cases. LD$_{50}$ values were calculated by the Reed & Muench method (Burleson et al., 1992) based on survival three weeks after inoculation. As shown in Table 1 below, the attenuated WN1415 strain (i.m. LD$_{50}$=0.9×106 pfu) is contrasted by the high virulence of NY99 strain (i.m. LD$_{50}$=17 pfu). Infection with NY99 uniformly resulted in rapidly progressing encephalitis accompanied by multiple paralysis and resolved by death often in less than 12 hours after onset of neurological symptoms. This is summarized by a short average survival time ("AST") with a rather little dependence on the virus dose and insignificant deviation among animals, as shown in Table 1. Permanent sequelae, such as hind limb paralysis, were often observed among survivors. In contrast, infection with lethal doses of WN1415 resolved in 2-3 days and was characterized by immobility, anorexia and a substantial weight loss, but paralytic symptoms were uncommon. Infection with lethal doses of WN1415 was characterized by overall longer AST, which also did not show a clear dependence on the virus dose but was characterized by a substantial deviation between animals (Table 1). The WN1415 virus was isolated from brains of all succumbed mice indicating that WN1415 is neuroinvasive when administered in high doses. Mice, which became symptomatic, apparently could not contain the infection and usually did not survive; those that have survived even high doses of WN1415 usually did not demonstrate visibly identifiable illness.

TABLE 1

Virulence of the parent viruses in mice

| WN1415[a] | D/T[b] | %[b] | AST | NY99[a] | D/T[b] | %[b] | AST |
|---|---|---|---|---|---|---|---|
| $2.6 \times 10^6$ | 3/6 | 50 | $10.7 \pm 2.5$ | — | — | — | — |
| $2.6 \times 10^5$ | 2/6 | 33 | $9.5 \pm 2.1$ | $8.8 \times 10^4$ | 6/6 | 100 | $7.5 \pm 0.8$ |
| $2.6 \times 10^4$ | 1/6 | 17 | $13.0 \pm 0.0$ | $8.8 \times 10^3$ | 6/6 | 100 | $8.0 \pm 1.3$ |
| $2.6 \times 10^3$ | 0/6 | 0 | N/A | $8.8 \times 10^2$ | 5/6 | 83 | $8.0 \pm 0.8$ |
| $2.6 \times 10^2$ | 0/6 | 0 | N/A | $8.8 \times 10^1$ | 5/6 | 83 | $8.0 \pm 1/4$ |
| $2.6 \times 10^2$ | 0/6 | 0 | N/A | $8.8 \times 10^0$ | 5/6 | 83 | $9.0 \pm 1.0$ |
| $LD_{50} = 0.9 \times 10^6$ pfu | | | | $LD_{50} = 1.7 \times 10^1$ pfu | | | |

[a]Intramuscular injection, pfu/mouse;
[b]Mortality at 2 weeks after inoculation As shown in Table 2, transfer of the NY99 structural protein genes into the genome of attenuated WN1415 did not result in transfer of the NY99 highly virulent phenotype, although an about 100-fold increase in virulence was observed based on values of $LD_{50}$.

less that 12 hours. Opposite to the two other chimeric viruses, the AST dependence on the dose of $WN956_{CME}$ was very similar to that of NY99 (compare AST in Table 1 and Table 2).

EXAMPLE 7

Immune Response to Chimeric Viruses

In this example, the immune response of 3-4 week old female Swiss Webster outbred mice that survived infection from Example 5 was investigated. More specifically, mice infected with chimeric viruses $NY99_{CME}$ and $NY99_{ME}$ were bled at 4 weeks after inoculation and immune sera were combined in each virus dose group to obtain averaged results. Endpoint dilution titers of NY99-specific IgG were determined by standard antibody-capture ELISA using the NY99 viral coating antigen produced from solubilized pelleted virions as described earlier (Yamshchikov et al., 2004). Readings that differ by two standard deviations from preimmune sera at the same dilution were considered positive. Titers of neutralizing antibodies were determined using NY99 virus and plaque reduction-neutralization titer (PRNT) microassay (constant virus-variable serum) as described (Yamshchikov et al., 2005; Yamshchikov et al., 2004). Briefly, confluent Vero cells in 96-well microplates were infected in duplicate with 50 pfu of NY99 in the presence of serially diluted immune sera, incubated for 24 hours, fixed and stained using WN-specific HMAF and ABC peroxidase-DAB procedure. Thus, the presence of virus-specific antibodies was evaluated by

TABLE 2

Virulence of the chimeric viruses in mice

| $NY99_{CME}$[a] | D/T[b] | %[b] | AST | $NY99_{ME}$[a] | D/T[b] | %[b] | AST | $WN956_{CME}$[a] | D/T[b] | %[b] | AST |
|---|---|---|---|---|---|---|---|---|---|---|---|
| $2.2 \times 10^6$ | 5/6 | 83 | $7.3 \pm 2.9$ | $5.75 \times 10^6$ | 4/6 | 67 | $7.8 \pm 2.2$ | $3.1 \times 10^6$ | 5/6 | 83 | $6.6 \pm 0.9$ |
| $2.2 \times 10^5$ | 3/6 | 50 | $7.7 \pm 0.6$ | $5.75 \times 10^5$ | 1/6 | 17 | $8.0 \pm 0.0$ | $3.1 \times 10^5$ | 6/6 | 100 | $6.8 \pm 0.8$ |
| $2.2 \times 10^4$ | 3/6 | 50 | $9.3 \pm 2.1$ | $5.75 \times 10^4$ | 6/6 | 100 | $9.7 \pm 1.5$ | $3.1 \times 10^4$ | 6/6 | 100 | $8.0 \pm 0.9$ |
| $2.2 \times 10^3$ | 3/6 | 50 | $10.0 \pm 0.0$ | $5.75 \times 10^3$ | 2/6 | 33 | $9.5 \pm 0.7$ | $3.1 \times 10^3$ | 6/6 | 100 | $8.5 \pm 0.5$ |
| $2.2 \times 10^2$ | 0/6 | 0 | — | $5.75 \times 10^2$ | 2/6 | 33 | $8.5 \pm 0.7$ | $3.1 \times 10^2$ | 6/6 | 100 | $8.2 \pm 0.4$ |
| $2.2 \times 10^1$ | 3/6 | 50 | $10.3 \pm 0.6$ | $5.75 \times 10^1$ | 4/6 | 67 | $11.5 \pm 2.4$ | $3.1 \times 10^1$ | 6/9 | 66 | $9.2 \pm 1.7$ |
| — | — | — | — | — | — | — | — | $3.1 \times 10^0$ | 0/3 | 0 | N/A |
| — | — | — | — | — | — | — | — | $3.1 \times 10^{-1}$ | 0/3 | 0 | N/A |
| $LD_{50} = 1.0 \times 10^4$ pfu | | | | $LD_{50} = 1.2 \times 10^4$ pfu | | | | $LD_{50} = 2.1 \times 10^1$ pfu- | | | |

[a]intramuscular injection, pfu/mouse;
[b]mortality at 2 weeks after inoculation Mice inoculated with either $NY99_{CME}$ and $NY99_{ME}$ chimeric viruses demonstrated scattered deaths with a lack of clear dependence on the virus dose, which significantly affected calculated $LD_{50}$. For either chimeric virus, however, the AST was more dependent on the virus dose. As shown in Table 2, in the upper dose range, the AST was closer to that after NY99 infection, but it gradually increased to resemble WN1415 in the lower dose range of chimeric viruses. Both chimeric viruses produced symptomatic patterns resembling either NY99 (paralytic encephalitis) or WN1415 (no paralytic symptoms).

Surprisingly, transfer of the structural protein genes from attenuated WN956 into the genome of virulent NY99 produced a chimeric virus that demonstrated essentially the same virulence in mice as parent NY99 (Table 2). Infection with $WN956_{CME}$ uniformly produced a rapidly developing paralytic encephalitis. Similarly to infection with NY99, a sudden onset of symptoms was followed by terminal resolution in ELISA with the NY99 viral antigen and in PRNT assays with NY99 virus. For comparison, the humoral immune response in mice that survived infection with WN1415 was also evaluated. A similar comparison with NY99 could not be done due to the low survival rate of infected mice. Some of the few animals that survived the lowest NY99 doses did not demonstrate any virus-specific immunity and likely did not experience infection.

As shown in Table 3, although animals demonstrated high titers of WN-specific IgG four weeks after inoculation with all tested viruses, mice inoculated with the chimeric viruses $NY99_{CME}$ and $NY99_{ME}$ developed, in general, a 4-fold to 10-fold stronger NY99-specific neutralizing humoral response. Comparison of NY99 neutralizing titers shown in Table 3 demonstrates that both chimeric viruses, even in the lowest dose groups, have induced titers of NY99 neutralizing antibodies superior to those caused by WN1415 immunization at the highest doses.

TABLE 3

Development of NY99-specific humoral immunity[a]

| WN1415[b] | | | NY99$_{CME}$[b] | | | NY99$_{ME}$[b] | | |
|---|---|---|---|---|---|---|---|---|
| dose | ELISA[c] | PRNT[d] | Dose | ELISA[c] | PRNT[d] | dose | ELISA[c] | PRNT[d] |
| $2.6 \times 10^6$ | 80000 | 320 | $2.2 \times 10^6$ | 10000 | 80 | $5.75 \times 10^6$ | 128000 | 1280 |
| $2.6 \times 10^5$ | 32000 | 120 | $2.2 \times 10^5$ | 320000 | 2133 | $5.75 \times 10^5$ | 128000 | 1493 |
| $2.6 \times 10^4$ | 32000 | 60 | $2.2 \times 10^4$ | 320000 | 1707 | $5.75 \times 10^4$ | ND | ND |
| $2.6 \times 10^3$ | 32000 | 2400 | $2.2 \times 10^3$ | 128000 | 640 | $5.75 \times 10^3$ | 128000 | 2987 |
| $2.6 \times 10^2$ | 32000 | 60 | $2.2 \times 10^2$ | 80000 | 640 | $5.75 \times 10^2$ | 32000 | 2133 |
| $2.6 \times 10^1$ | 0 | 0 | $2.2 \times 10^1$ | 80000 | 320 | $5.75 \times 10^1$ | 32000 | 960 |

[a]serum samples were collected at 4 weeks post-inoculation and combined for each virus dose group
[b]immunizing virus administered i.m. at the specified doses as determined by back-titration
[c]endpoint dilution titers with the NY99 viral coating antigen
[d]endpoint dilution plaque-reduction neutralization titers with NY99 virus Next, the presence of neutralizing antibodies that protected against infection with virulent NY99 was tested. Mice that survived the primary infection were challenged at four weeks with 100 $LD_{50}$ of NY99 virus intramuscularly and were observed for an additional three weeks. All animals that demonstrated the presence of neutralizing antibodies survived subsequent challenge with 100$LD_{50}$ of NY99. There were no survivors in the lowest WN1415 dose group as well as among control unimmunized mice.

All publications mentioned herein are incorporated herein by reference to describe the methods and/or materials in connection with which the publications are cited.

Beasley, D. W., Li, L., Suderman, M. T., and Barrett, A. D. (2001). West Nile virus strains differ in mouse neurovirulence and binding to mouse or human brain membrane receptor preparations. Ann, N Y Acad. Sci. 951, 332-335.

Beasley, D. W., Li, L., Suderman, M. T., and Barrett, A. D. (2002). Mouse neuroinvasive phenotype of West Nile virus strains varies depending upon virus genotype. Virology 296, 17-23.

Beasley, D. W. C., Whiteman, M. C., Zhang, S., Huang, C. Y.-H., Schneider, B. S., Smith, D. R., Gromowski, G. D., Higgs, S., Kinney, R. M., and Barrett, A. D. T. (2005). Envelope Protein Glycosylation Status Influences Mouse Neuroinvasion Phenotype of Genetic Lineage 1 West Nile Virus Strains. J. Virol. 79, 8339-8347.

Berthet, F. X., Zeller, H. G., Drouet, M. T., Rauzier, J., Digoutte, J. P., and Deubel, V. (1997). Extensive nucleotide changes and deletions within the envelope glycoprotein gene of Euro-African West Nile viruses. J Gen Virol 78, 2293-2297.

Burleson, F. G., Chambers, T. M., and Wiedbrauk, D. L. (1992). "Virology: A Laboratory Manual." Academic Press Inc., San Diego, New York, Boston, London, Sydney, Tokyo, Toronto.

Butrapet, S., Huang, C. Y., Pierro, D. J., Bhamarapravati, N., Gubler, D. J., and Kinney, R. M. (2000). Attenuation markers of a candidate dengue type 2 vaccine virus, strain 16681 (PDK-53), are defined by mutations in the 5' noncoding region and nonstructural proteins 1 and 3. J. Virol. 74, 3011-3019.

CDC (2005). 2004 West Nile Virus Activity in the United States.

Cecilia, D., and Gould, E. A. (1991). Nucleotide changes responsible for loss of neuroinvasiveness in Japanese encephalitis virus neutralization-resistant mutants. Virology 181, 70-77.

Chambers, T. J., Halevy, M., Nestorowicz, A., Rice, C. M., and Lustig, S. (1998). West Nile virus envelope proteins: nucleotide sequence analysis of strains differing in mouse neuroinvasiveness. J Gen Virol. 79, 2375-2380.

Chambers, T. J., Nestorowicz, A., Mason, P. W., and Rice, C. M. (1999). Yellow fever/Japanese encephalitis chimeric viruses: construction and biological properties. J. Virol. 73, 3095-3101.

Chu, J. J., and Ng, M. L. (2003). The mechanism of cell death during West Nile virus infection is dependent on initial infectious dose. J Gen Virol. 84, 3305-3314.

Co, M. D., Terajima, M., Cruz, J., Ennis, F. A., and Rothman, A. L. (2002). Human cytotoxic T lymphocyte responses to live attenuated 17D yellow fever vaccine: identification of HLA-B35-restricted CTL epitopes on nonstructural proteins NS1, NS2b, NS3, and the structural protein E. Virology 293, 151-163.

Duarte dos Santos, C. N., Frenkiel, M. P., Courageot, M. P., Fernando, S. R. C., Vazeille-Falcoz, M. C., Wien, M. W., Rey, F. A., Deubel, V., and Despres, P. (2000). Determinants in the Envelope E Protein and Viral RNA Helicase NS3 That Influence the Induction of Apoptosis in Response to Infection with Dengue Type 1 Virus. Virology 274, 292-308.

Dunster, L. M., Wang, H., Ryman, K. D., Miller, B. R., Watowich, S. J., Minor, P. D., and Barrett, A. D. (1999). Molecular and biological changes associated with HeLa cell attenuation of wild-type yellow fever virus. Virology 261, 309-318.

Flatau, E., Kohn, D., Daher, O., and Varsano, N. (1981). West Nile fever encephalitis. Isr J. Med. Sci. 17, 1057-1059.

Gualano, R. C., Pryor, M. J., Cauchi, M. R., Wright, P. J., and Davidson, A. D. (1998). Identification of a major determinant of mouse neurovirulence of dengue virus type 2 using stably cloned genomic-length cDNA. J. Gen. Virol. 79, 437-446.

Hanna, S. L., Pierson, T. C., Sanchez, M. D., Ahmed, A. A., Murtadha, M. M., and Doms, R. W. (2005). N-Linked Glycosylation of West Nile Virus Envelope Proteins Influences Particle Assembly and Infectivity. J. Virol. 79, 13262-13274.

Hasegawa, H., Yoshida, M., Shiosaka, T., Fujita, S., and Kobayashi, Y. (1992). Mutations in the envelope protein of Japanese encephalitis virus affect entry into cultured cells and virulence in mice. Virology 191, 158-165.

Holzmann, H., Heinz, F. X., Mandl, C. W., Guirakhoo, F., and Kunz, C. (1990). A single amino acid substitution in envelope protein E of tick-borne encephalitis virus leads to attenuation in the mouse model. J. Virol. 64, 5156-5159.

Holzmann, H., Stiasny, K., Ecker, M., Kunz, C., and Heinz, F. X. (1997). Characterization of monoclonal antibody-escape mutants of tick-borne encephalitis virus with reduced neuroinvasiveness in mice. *J. Gen. Virol.* 78, 31-37.

Jiang, W. R., Lowe, A., Higgs, S., Reid, H., and Gould, E. A. (1993). Single amino acid codon changes detected in louping ill virus antibody-resistant mutants with reduced neurovirulence. *J. Gen. Virol.* 74, 931-935.

Kahler, S. C. (2003). APHIS: West Nile virus vaccine safe for use. *J. Am. Vet. Med. Assoc.* 223, 416-418.

Lai, C. J., and Monath, T. P. (2003). Chimeric flaviviruses: novel vaccines against dengue fever, tick-borne encephalitis, and Japanese encephalitis. *Adv. Virus Res.* 61, 469-509.

Lanciotti, R. S., Ebel, G. D., Deubel, V., Kerst, A. J., Murri, S., Meyer, R., Bowen, M., McKinney, N., Morrill, W. E., Crabtree, M. B., Kramer, L. D., and Roehrig, J. T. (2002). Complete genome sequences and phylogenetic analysis of West Nile virus strains isolated from the United States, Europe, and the Middle East. *Virology* 298, 96-105.

Lanciotti, R. S., Roehrig, J. T., Deubel, V., Smith, J., Parker, M., Steele, K., Crise, B., Volpe, K. E., Crabtree, M. B., Scherret, J. H., Hall, R. A., MacKenzie, J. S., Cropp, C. B., Panigrahy, B., Ostlund, E., Schmitt, B., Malkinson, M., Banet, C., Weissman, J., Komar, N., Savage, H. M., Stone, W., McNamara, T., and Gubler, D. J. (1999). Origin of the West Nile virus responsible for an outbreak of encephalitis in the northeastern United States. *Science* 286, 2333-2337.

Lindenbach, B. D., and Rice, C. M. (2001). Flaviviridae: The Viruses and Their Replication. $4^{th}$ ed. In "Fields Virology" (D. M. Knipe, P. M. Howley, D. E. Griffin, A. M. Martin, R. A. Lamb, B. Roizman, and S. E. Strauss, Eds.), Vol. 1, pp. 991-1041. 2 vols. Lippincott Williams & Wilkins, Philadelphia.

Lobigs, M., Arthur, C. E., Mullbacher, A., and Blanden, R. V. (1994). The flavivirus nonstructural protein NS3 is a dominant source of cytotoxic T cell peptide determinants. *Virology* 202, 195-201.

Mathew, A., Kurane, I., Rothman, A. L., Zeng, L. L., Brinton, M. A., and Ennis, F. A. (1996). Dominant recognition by human CD8+ cytotoxic T lymphocytes of dengue virus nonstructural proteins NS3 and NS 1.2a. *J. Clin. Invest* 98, 1684-1691.

McMinn, P. C. (1997). The molecular basis of virulence of the encephalitogenic flaviviruses. *J. Gen. Virol.* 78, 2711-2722.

Mishin, V. P., Cominelli, F., and Yamshchikov, V. F. (2001). A 'minimal' approach in design of flavivirus infectious DNA. *Virus Res.* 81, 113-123.

Monath, T. P. (2001). Prospects for development of a vaccine against the West Nile virus. *Ann, NY Acad. Sci.* 951, 1-12.

Monath, T. P., and Heinz, F. X. (1996). Flaviviruses. 3d ed. In "Fields Virology" (B. N. Fields, D. M. Knipe, P. M. Howley, R. M. Chanock, J. L. Melnick, T. P. Monath, B. Roizman, and S. E. & Strauss, Eds.), Vol. 1, pp. 961-1034. 2 vols. Lippincott-Raven, Philadelphia.

Murgue, B., Murri, S., Triki, H., Deubel, V., and Zeller, H. G. (2001). West Nile in the Mediterranean basin: 1950-2000. *Ann, NY Acad. Sci.* 951, 117-126.

Muylaert, I. R., Chambers, T. J., Galler, R., and Rice, C. M. (1996). Mutagenesis of the N-linked glycosylation sites of the yellow fever virus NS1 protein: effects on virus replication and mouse neurovirulence. *Virology* 222, 159-168.

Ng, T., Hathaway, D., Jennings, N., Champ, D., Chiang, Y. W., and Chu, H. J. (2003). Equine vaccine for West Nile virus. *Dev. Biol. (Basel)* 114, 221-227.

Ni, H., Chang, G. J., Xie, H., Trent, D. W., and Barrett, A. D. (1995). Molecular basis of attenuation of neurovirulence of wild-type Japanese encephalitis virus strain SA14. *J. Gen. Virol.* 76, 409-413.

Nusbaum, K. E., Wright, J. C., Johnston, W. B., Allison, A. B., Hilton, C. D., Staggs, L. A., Stallknecht, D. E., and Shelnutt, J. L. (2003). Absence of humoral response in flamingos and red-tailed hawks to experimental vaccination with a killed West Nile virus vaccine. *Avian Dis.* 47, 750-752.

Okamoto, Y., Kurane, I., Leporati, A. M., and Ennis, F. A. (1998). Definition of the region on NS3 which contains multiple epitopes recognized by dengue virus serotype-crossreactive and flavivirus-cross-reactive, HLA-DPw2-restricted CD4+ T cell clones. *J. Gen. Virol.* 79, 697-704.

Parrish, C. R., Coia, G., Hill, A., Mullbacher, A., Westaway, E. G., and Blanden, R. V. (1991). Preliminary analysis of murine cytotoxic T cell responses to the proteins of the flavivirus Kunjin using vaccinia virus expression. *J. Gen. Virol.* 72, 1645-1653.

Pletnev, A. G., Bray, M., Huggins, J., and Lai, C. J. (1992). Construction and characterization of chimeric tick-borne encephalitis/dengue type 4 viruses. *Proc. Natl. Acad. Sci. USA* 89, 10532-10536.

Pletnev, A. G., Bray, M., and Lai, C. J. (1993). Chimeric tick-borne encephalitis and dengue type 4 viruses: effects of mutations on neurovirulence in mice. *J. Virol.* 67, 4956-4963.

Pletnev, A. G., Putnak, R., Speicher, J., Wagar, E. J., and Vaughn, D. W. (2002). West Nile virus/dengue type 4 virus chimeras that are reduced in neurovirulence and peripheral virulence without loss of immunogenicity or protective efficacy. *Proc. Natl. Acad. Sci. USA* 99, 3036-3041.

Price, W. H., and O'Leary, W. (1967). Geographic variation in the antigenic character of West Nile virus. *American Journal of Epidemiology* 85, 84-86.

Qu, L., McMullan, L. K., and Rice, C. M. (2001). Isolation and characterization of noncytopathic pestivirus mutants reveals a role for nonstructural protein NS4B in viral cytopathogenicity. *J. Virol.* 75, 10651-10662.

Ramanathan, M. P., Chambers, J. A., Pankhong, P., Chattergoon, M., Attatippaholkun, W., Dang, K., Shah, N., and Weiner, D. B. (2005). Host cell killing by the West Nile Virus NS2B-NS3 proteolytic complex: NS3 alone is sufficient to recruit caspase-8-based apoptotic pathway. *Virology In Press.*

Roehrig, J. T., Layton, M., Smith, P., Campbell, G. L., Nasci, R., and Lanciotti, R. S. (2002). The emergence of West Nile virus in North America: ecology, epidemiology, and surveillance. *Curr. Top Microbiol. Immunol.* 267, 223-240.

Rossi, S. L., Zhao, Q., O'Donnell, V. K., and Mason, P. W. (2005). Adaptation of West Nile virus replicons to cells in culture and use of replicon-bearing cells to probe antiviral action. *Virology* 331, 457-470.

Sambrook, J., and Russell, D. W. (2001). In "Molecular Cloning: A Laboratory Manual." Third edition. ed. 3 vols. Cold Spring Harbor Laboratory Press, New York.

Savage, H. M., Ceianu, C., Nicolescu, G., Karabatsos, N., Lanciotti, R., Vladimirescu, A., Laiv, L., Ungureanu, A., Romanca, C., and Tsai, T. F. (1999). Entomologic and avian investigations of an epidemic of West Nile fever in Romania in 1996, with serologic and molecular characterization of a virus isolate from mosquitoes. *Am. J. Trop. Med. Hyg.* 61, 600-611.

Shi, P. Y., Tilgner, M., Lo, M. K., Kent, K. A., and Bernard, K. A. (2002). Infectious cDNA clone of the epidemic West Nile virus from New York City. *J. Virol.* 76, 5847-5856.

Shirato, K., Miyoshi, H., Goto, A., Ako, Y., Ueki, T., Kariwa, H., and Takashima, I. (2004). Viral envelope protein glycosylation is a molecular determinant of the neuroinvasiveness of the New York strain of West Nile virus. *J. Gen. Virol.* 85, 3637-3645.

Smithburn, K. C., Hughes, T. P., Burke, A. V., and Paul, J. H. (1940). A neurotropic virus isolated from the blood of a native of Uganda. *Am. J. Trop. Med. Hyg.* 20, 471-492.

Solomon, T., and Vaughn, D. W. (2002). Pathogenesis and clinical features of Japanese encephalitis and West Nile virus infections. *Curr. Top. Microbiol. Immunol.* 267, 171-194.

Spaulding, A. C., Kurane, I., Ennis, F. A., and Rothman, A. L. (1999). Analysis of murine CD8(+) T-cell clones specific for the Dengue virus NS3 protein: flavivirus crossactivity and influence of infecting serotype. *J. Virol.* 73, 398-403.

Tesh, R. B., Arroyo, J., Travassos Da Rosa, A. P., Guzman, H., Xiao, S. Y., and Monath, T. P. (2002). Efficacy of Killed Virus Vaccine, Live Attenuated Chimeric Virus Vaccine, and Passive Immunization for Prevention of West Nile virus Encephalitis in Hamster Model. *Emerg. Infect. Dis,* 8, 1392-1397.

Wengler, G., Castle, E., Leidner, U., and Nowak, T. (1985). Sequence analysis of the membrane protein V3 of the flavivirus West Nile virus and of its gene. *Virology* 147, 264-274.

Xiao, S. Y., Guzman, H., Zhang, H., Travassos da Rosa, A. P., and Tesh, R. B. (2001). West Nile virus infection in the golden hamster (*Mesocricetus auratus*): a model for West Nile encephalitis. *Emerg. Infect. Dis.* 7, 714-721.

Xie, H., Ryman, K. D., Campbell, G. A., and Barrett, A. D. (1998). Mutation in NS5 protein attenuates mouse neurovirulence of yellow fever 17D vaccine virus. *J. Gen. Virol.* 79, 1895-1899.

Yamshchikov, G., Borisevich, V., Kwok, C. W., Nistler, R., Kohlmeier, J., Seregin, A., Chaporgina, E., Benedict, S., and Yamshchikov, V. (2005). The suitability of yellow fever and Japanese encephalitis vaccines for immunization against West Nile virus. *Vaccine* 23, 4785-4792.

Yamshchikov, G., Borisevich, V., Seregin, A., Chaporgina, E., Mishina, M., Mishin, V., Kwok, C. W., and Yamshchikov, V. (2004). An attenuated West Nile prototype virus is highly immunogenic and protects against the deadly NY99 strain: a candidate for live WN vaccine development. *Virology* 330, 304-312.

Yamshchikov, V., Mishin, V., and Cominelli, F. (2001a). A new strategy in design of +RNA virus infectious clones enabling their stable propagation in *E. coli. Virology* 281, 272-280.

Yamshchikov, V. F., and Compans, R. W. (1993). Regulation of the late events in flavivirus protein processing and maturation. *Virology* 192, 38-51.

Yamshchikov, V. F., and Compans, R. W. (1995). Formation of the flavivirus envelope: role of the viral NS2B-NS3 protease. *J. Virol.* 69, 1995-2003.

Yamshchikov, V. F., Trent, D. W., and Compans, R. W. (1997). Upregulation of signalase processing and induction of prM-E secretion by the flavivirus NS2B-NS3 protease: roles of protease components. *J. Virol.* 71, 4364-4371.

Yamshchikov, V. F., Wengler, G., Perelygin, A. A., Brinton, M. A., and Compans, R. W. (2001b). An infectious clone of the West Nile flavivirus. *Virology* 281, 294-304.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A recombinant genetic construct, adapted to encode a full-length West Nile viral genome, comprising a nucleic acid region encoding a structural protein of a first West Nile virus and a nucleic acid region encoding a non-structural protein of a second West Nile virus, wherein said second West Nile virus is a different virus from said first West Nile virus.

2. The recombinant genetic construct of claim 1 wherein said first West Nile virus and said second West Nile virus are independently selected from the group consisting of strains NY99 and WN1415.

3. The recombinant genetic construct of claim 1 wherein the nucleic acid region encoding a structural protein of said first West Nile virus encodes the premembrane (prM) and envelope (E) proteins of the NY99 virus and the nucleic acid region encoding a non-structural protein of said second West Nile virus encodes the NS 1, NS2A, NS2B, NS3, NS4A, NS4B and NS5 proteins of the WN1415 virus.

4. The recombinant genetic construct of claim 3 wherein the nucleic acid region encoding a structural protein of said first West Nile virus also encodes the capsid (C) protein of the NY99 virus.

5. The recombinant genetic construct of claim 1 wherein the nucleic acid region encoding a structural protein of said first West Nile virus encodes the capsid (C), premembrane (prM) and envelope (E) proteins of the WN1415 virus and the nucleic acid region encoding a non-structural protein of said second West Nile virus encodes the NS1, NS2A, NS2B, NS3, NS4A, NS4B and NS5 proteins of the NY99 virus.

6. The recombinant genetic construct of claim 1 wherein said nucleic acid region encoding a structural protein of said first West Nile virus is derived from a more virulent West Nile virus than said nucleic acid region encoding a non-structural protein of said second West Nile virus, which is less virulent.

7. The recombinant genetic construct of claim 1 wherein the nucleic acid region encoding a structural protein encodes an E protein that is not glycosylated or contains a mutated glycosylation site.

8. The recombinant genetic construct of claim 1 further comprising at least one open reading frame interrupting intron downstream from the first occurrence of AUG in the cluster of in-frame AUG codons occurring at the end of the E gene.

9. The recombinant genetic construct of claim 8 wherein said at least one open reading frame interrupting intron is located at position 2210 or 2384 of the West Nile genome.

10. The recombinant genetic construct of claim 1 further comprising at least one open reading frame interrupting intron in the area encompassing the 3' end of the NS1 gene and 5' end of the NS2A gene.

11. The recombinant genetic construct of claim 1 further comprising a vector.

12. The recombinant genetic construct of claim 11 wherein said vector is a plasmid.

13. The recombinant genetic construct of claim 12 wherein said plasmid comprises DNA encoding an infectious (+) RNA molecule under the control of a eukaryotic promoter.

14. The recombinant genetic construct of claim 13 wherein said eukaryotic promoter comprises a CMV promoter.

15. A host cell stably or transiently transfected with the recombinant genetic construct of claim 1.

16. An infectious West Nile virus comprising a full-length West Nile viral genome, comprising a nucleic acid region encoding a structural protein of a first West Nile virus and a nucleic acid region encoding a non-structural protein of a second West Nile virus, wherein said second West Nile virus is a different virus from said first West Nile virus.

17. An immunogenic composition against West Nile virus comprising a therapeutically effective amount of the recombinant genetic construct of claim 1 and a pharmaceutically acceptable carrier.

18. A method of immunizing a subject against West Nile virus comprising the step of administering to a subject the immunogenic composition of claim 17.

19. The recombinant genetic construct of claim 1 wherein the nucleic acid region encoding a structural protein of said first West Nile virus encodes the premembrane (prM) and envelope (E) proteins of a first West Nile virus and the nucleic acid region encoding a non-structural protein of said second West Nile virus encodes the NS1, NS2A, NS2B, NS3, NS4A, NS4B, and NS5 proteins of a second West Nile virus, and further comprising at least one open reading frame interrupting intron downstream from the first occurrence of AUG in the cluster of in-frame AUG codons occurring at the end of the E gene, at least one intron is located at position 2210, 2384, or 3472 of the West Nile genome.

20. The recombinant genetic construct of claim 19 wherein said first West Nile virus is the NY99 virus, and said second West Nile virus is the WN1415 virus.

21. The recombinant genetic construct of claim 8 further comprising at least one additional open reading frame interrupting intron in the area encompassing the 3' end of the NS1 gene and 5' end of the NS2A gene.

22. The recombinant genetic construct of claim 9 further comprising at least one additional open reading frame interrupting intron at position 3472 of West Nile Virus genome.

23. The recombinant genetic construct of claim 10 wherein the at least one open reading frame interrupting intron at position 3472 of West Nile Virus genome.

* * * * *